US012290230B2

(12) United States Patent
Mai et al.

(10) Patent No.: US 12,290,230 B2
(45) Date of Patent: May 6, 2025

(54) METHOD, APPARATUS, AND SYSTEM FOR AUTOMATIC AND ADAPTIVE WIRELESS MONITORING AND TRACKING

(71) Applicants: Chao-Lun Mai, Cambridge, MA (US); Jeng-Feng Lee, Cambridge, MA (US); Hung-Quoc Duc Lai, Parkville, MD (US); Dan Bugos, Washington, DC (US); Hangfang Zhang, Greenbelt, MD (US); Beibei Wang, Clarksville, MD (US); Oscar Chi-Lim Au, San Jose, CA (US); K. J. Ray Liu, Potomac, MD (US)

(72) Inventors: Chao-Lun Mai, Cambridge, MA (US); Jeng-Feng Lee, Cambridge, MA (US); Hung-Quoc Duc Lai, Parkville, MD (US); Dan Bugos, Washington, DC (US); Hangfang Zhang, Greenbelt, MD (US); Beibei Wang, Clarksville, MD (US); Oscar Chi-Lim Au, San Jose, CA (US); K. J. Ray Liu, Potomac, MD (US)

(73) Assignee: ORIGIN RESEARCH WIRELESS, INC., Rockville, MD (US)

( * ) Notice: Subject to any disclaimer, the term of this patent is extended or adjusted under 35 U.S.C. 154(b) by 0 days.

(21) Appl. No.: 17/537,432

(22) Filed: Nov. 29, 2021

(65) Prior Publication Data

US 2022/0096003 A1 Mar. 31, 2022

Related U.S. Application Data

(60) Division of application No. 17/019,273, filed on Sep. 13, 2020, now abandoned, which is a
(Continued)

(51) Int. Cl.
*A61B 5/08* (2006.01)
*A61B 5/00* (2006.01)
(Continued)

(52) U.S. Cl.
CPC .......... *A61B 5/4818* (2013.01); *A61B 5/0816* (2013.01); *A61B 5/7253* (2013.01); *H04B 1/713* (2013.01); *H04L 25/0226* (2013.01)

(58) Field of Classification Search
CPC ... A61B 5/0816; A61B 5/4818; A61B 5/7253; A61B 2503/04; A61B 2503/12;
(Continued)

(56) References Cited

U.S. PATENT DOCUMENTS 10,498,467 B1 * 12/2019 Ravkine ............ H04W 52/0238
10,499,364 B1 * 12/2019 Ravkine ............ H04W 64/006
(Continued)

FOREIGN PATENT DOCUMENTS

CN 112346050 * 2/2021 ........... A61B 5/1117

OTHER PUBLICATIONS

Liu et al., "Tracking Vital Signs During Sleep Leveraging Off-the-shelf WiFi", Jun. 2015, MobiHoc'15, pp. 267-276 (Year: 2015).*
(Continued)

*Primary Examiner* — Zhiyu Lu

(57) ABSTRACT

Methods, apparatus and systems for wireless monitoring and tracking are described. In one example, a described method of a wireless monitoring system comprises: transmitting a wireless signal that is impacted by a wireless multipath channel in a venue and a modulation of an object undergoing a motion in the venue, to obtain a set of channel information (CI) of the wireless multipath channel; performing a monitoring task by monitoring the object and the motion; determining a plurality of admissible system states of the wireless monitoring system, wherein each admissible system state is
(Continued)

associated with a respective setting of at least one of: the wireless signal, a series of sounding signals in the wireless signal, or the monitoring task; choosing one of the admissible system states to be a system state of the wireless monitoring system based on the monitoring task; and applying a setting associated with the chosen admissible system state to the wireless monitoring system.

12 Claims, 9 Drawing Sheets

Related U.S. Application Data continuation-in-part of application No. 16/127,151, filed on Sep. 10, 2018, now Pat. No. 11,012,285, which is a continuation-in-part of application No. PCT/US2017/021963, filed on Mar. 10, 2017, said application No. 17/019,273 is a continuation-in-part of application No. 16/127,748, filed on Sep. 9, 2018, now Pat. No. 10,833,912, which is a continuation-in-part of application No. PCT/US2017/015909, filed on Jan. 31, 2017, said application No. 17/019,273 is a continuation-in-part of application No. 15/861,422, filed on Jan. 3, 2018, now Pat. No. 11,025,475, and a continuation-in-part of application No. 16/667,648, filed on Oct. 29, 2019, now Pat. No. 11,035,940, and a continuation-in-part of application No. 16/667,757, filed on Oct. 29, 2019, now abandoned, and a continuation-in-part of application No. 16/790,610, filed on Feb. 13, 2020, now Pat. No. 11,928,894, and a continuation-in-part of application No. 16/790,627, filed on Feb. 13, 2020, now Pat. No. 11,397,258, and a continuation-in-part of application No. 16/798,337, filed on Feb. 22, 2020, now Pat. No. 10,845,463, and a continuation-in-part of application No. 16/798,343, filed on Feb. 22, 2020, now Pat. No. 11,340,345, and a continuation-in-part of application No. 16/870,996, filed on May 10, 2020, now Pat. No. 10,866,302, and a continuation-in-part of application No. 16/871,000, filed on May 10, 2020, now Pat. No. 11,500,056, and a continuation-in-part of application No. 16/871,004, filed on May 10, 2020, now Pat. No. 12,046,040, and a continuation-in-part of application No. 16/871,006, filed on May 10, 2020, now Pat. No. 11,408,978, and a continuation-in-part of application No. 16/909,913, filed on Jun. 23, 2020, now abandoned, and a continuation-in-part of application No. 16/909,940, filed on Jun. 23, 2020, now Pat. No. 11,391,830, and a continuation-in-part of application No. 16/945,827, filed on Aug. 1, 2020, now Pat. No. 11,444,710, and a continuation-in-part of application No. 16/945,837, filed on Aug. 1, 2020, now Pat. No. 11,439,344, and a continuation-in-part of application No. 15/326,112, filed as application No. PCT/US2015/041037 on Jul. 17, 2015, now abandoned.

(60) Provisional application No. 62/900,565, filed on Sep. 15, 2019, provisional application No. 62/902,357, filed on Sep. 18, 2019, provisional application No. 62/950,093, filed on Dec. 18, 2019, provisional application No. 62/977,326, filed on Feb. 16, 2020, provisional application No. 62/980,206, filed on Feb. 22, 2020, provisional application No. 62/981,387, filed on Feb. 25, 2020, provisional application No. 62/984,737, filed on Mar. 3, 2020, provisional application No. 63/001,226, filed on Mar. 27, 2020, provisional application No. 63/038,037, filed on Jun. 11, 2020.

(51) Int. Cl.
*H04B 1/713* (2011.01)
*H04L 25/02* (2006.01)

(58) Field of Classification Search
CPC ..... A61B 5/0022; A61B 5/0205; A61B 5/113; A61B 5/7264; H04B 1/713; H04L 1/0026; H04L 1/24; H04L 25/0226; H04L 27/362; H04L 5/0048; H04L 25/0204; H04L 25/0224; G16H 50/00
See application file for complete search history.

(56) References Cited

U.S. PATENT DOCUMENTS

2018/0097597 A1* 4/2018 Legg ................... H04W 72/042
2019/0341988 A1* 11/2019 Schelstraete ......... H04B 7/0626
2021/0067212 A1* 3/2021 Pierrugues ......... H04B 17/3913

OTHER PUBLICATIONS

Liu et al., "Wi-Sleep: Contactless Sleep Monitoring via WiFi Signals", Dec. 2014, IEEE, pp. 346-355 (Year: 2014).*
Ma et al., "A Survey on Wi-Fi based Contactless Activity Recognition", 2016, IEEE, pp. 1086-1091 (Year: 2016).*
Khalili et al., "Wi-Fi Sensing: Applications and Challenges", 2019, arXiv.org (Year: 2019).*
Xu et al., "Attention-based Walking Gait and Direction Recognition in Wi-Fi Networks", 2019. arXov.org (Year: 2019).*
Tino et al. "Chapter 6—Finite State Machines and Recurrent Neural Networks—Automata and Dynamical Systems Approaches" from "Neural Networks and Pattern Recognition", 1998, pp. 171-219 (Year: 1998).*

\* cited by examiner

METHOD, APPARATUS, AND SYSTEM FOR AUTOMATIC AND ADAPTIVE WIRELESS MONITORING AND TRACKING

CROSS-REFERENCE TO RELATED APPLICATIONS

The present application is a Divisional Application of U.S. patent application Ser. No. 17/019,273, filed on Sep. 13, 2020, which incorporated each of the following applications by reference in its entirety: U.S. patent application Ser. No. 17/019,271, filed on Sep. 13, 2020, and U.S. patent application Ser. No. 17/019,270, filed on Sep. 13, 2020.

The U.S. patent application Ser. No. 17/019,273 incorporated by reference the entirety of the disclosures of, and claimed priority to, each of the following cases:

(a) U.S. patent application Ser. No. 15/326,112, entitled "WIRELESS POSITIONING SYSTEMS", filed on Jan. 13, 2017,
  (1) which is a national stage entry of PCT patent application PCT/US2015/041037, entitled "WIRELESS POSITIONING SYSTEMS", filed on Jul. 17, 2015, published as WO 2016/011433A2 on Jan. 21, 2016,
(b) U.S. patent application Ser. No. 16/127,151, entitled "METHODS, APPARATUS, SERVERS, AND SYSTEMS FOR VITAL SIGNS DETECTION AND MONITORING", filed on Sep. 10, 2018,
  (1) which is a continuation-in-part of PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
(c) U.S. patent application Ser. No. 16/125,748, entitled "METHODS, DEVICES, SERVERS, APPARATUS, AND SYSTEMS FOR WIRELESS INTERNET OF THINGS APPLICATIONS", filed on Sep. 9, 2018,
  (1) which is a continuation-in-part of PCT patent application PCT/US2017/015909, entitled "METHODS, DEVICES, SERVERS, APPARATUS, AND SYSTEMS FOR WIRELESS INTERNET OF THINGS APPLICATIONS", filed on Jan. 31, 2017, published as WO2017/155634A1 on Sep. 14, 2017,
(d) U.S. patent application Ser. No. 15/861,422, entitled "METHOD, APPARATUS, SERVER, AND SYSTEMS OF TIME-REVERSAL TECHNOLOGY", filed on Jan. 3, 2018,
(e) U.S. Provisional Patent application 62/900,565, entitled "QUALIFIED WIRELESS SENSING SYSTEM", filed on Sep. 15, 2019,
(f) U.S. Provisional Patent application 62/902,357, entitled "METHOD, APPARATUS, AND SYSTEM FOR AUTOMATIC AND OPTIMIZED DEVICE-TO-CLOUD CONNECTION FOR WIRELESS SENSING", filed on Sep. 18, 2019,
(g) U.S. patent application Ser. No. 16/667,648, entitled "METHOD, APPARATUS, AND SYSTEM FOR WIRELESS PROXIMITY AND PRESENCE MONITORING", filed on Oct. 29, 2019,
(h) U.S. patent application Ser. No. 16/667,757, entitled "METHOD, APPARATUS, AND SYSTEM FOR HUMAN IDENTIFICATION BASED ON HUMAN RADIO BIOMETRIC INFORMATION", filed on Oct. 29, 2019,
(i) U.S. Provisional Patent application 62/950,093, entitled "METHOD, APPARATUS, AND SYSTEM FOR TARGET POSITIONING", filed on Dec. 18, 2019,
(j) U.S. patent application Ser. No. 16/790,610, entitled "METHOD, APPARATUS, AND SYSTEM FOR WIRELESS GAIT RECOGNITION", filed Feb. 13, 2020,
(k) U.S. patent application Ser. No. 16/790,627, entitled "METHOD, APPARATUS, AND SYSTEM FOR OUTDOOR TARGET TRACKING", filed Feb. 13, 2020.
(l) U.S. Provisional Patent application 62/977,326, entitled "METHOD, APPARATUS, AND SYSTEM FOR AUTOMATIC AND ADAPTIVE WIRELESS MONITORING AND TRACKING", filed on Feb. 16, 2020,
(m) U.S. patent application Ser. No. 16/798,337, entitled "METHOD, APPARATUS, AND SYSTEM FOR WIRELESS OBJECT SCANNING", filed Feb. 22, 2020,
(n) U.S. patent application Ser. No. 16/798,343, entitled "METHOD, APPARATUS, AND SYSTEM FOR WIRELESS OBJECT TRACKING", filed Feb. 22, 2020,
(o) U.S. Provisional Patent application 62/980,206, entitled "METHOD, APPARATUS, AND SYSTEM FOR WIRELESS SENSING", filed on Feb. 22, 2020,
(p) U.S. Provisional Patent application 62/981,387, entitled "METHOD, APPARATUS, AND SYSTEM FOR VEHICLE WIRELESS MONITORING", filed on Feb. 25, 2020,
(q) U.S. Provisional Patent application 62/984,737, entitled "METHOD, APPARATUS, AND SYSTEM FOR IMPROVED WIRELESS MONITORING", filed on Mar. 3, 2020,
(r) U.S. Provisional Patent application 63/001,226, entitled "METHOD, APPARATUS, AND SYSTEM FOR IMPROVED WIRELESS MONITORING AND USER INTERFACE", filed on Mar. 27, 2020,
(s) U.S. patent application Ser. No. 16/870,996, entitled "METHOD, APPARATUS, AND SYSTEM FOR WIRELESS INERTIAL MEASUREMENT", filed on May 10, 2020,
(t) U.S. patent application Ser. No. 16/871,000, entitled "METHOD, APPARATUS, AND SYSTEM FOR WIRELESS TRACKING WITH GRAPH-BASED PARTICLE FILTERING", filed on May 10, 2020,
(u) U.S. patent application Ser. No. 16/871,004, entitled "METHOD, APPARATUS, AND SYSTEM FOR PEOPLE COUNTING AND RECOGNITION BASED ON RHYTHMIC MOTION MONITORING", filed on May 10, 2020,
(v) U.S. patent application Ser. No. 16/871,006, entitled "METHOD, APPARATUS, AND SYSTEM FOR VITAL SIGNS MONITORING USING HIGH FREQUENCY WIRELESS SIGNALS", filed on May 10, 2020,
(w) U.S. Provisional Patent application 63/038,037, entitled "METHOD, APPARATUS, AND SYSTEM FOR MOTION LOCALIZATION, WALKING DETECTION AND DEVICE QUALIFICATION", filed on Jun. 11, 2020,
(x) U.S. patent application Ser. No. 16/909,913, entitled "METHOD, APPARATUS, AND SYSTEM FOR IMPROVING TOPOLOGY OF WIRELESS SENSING SYSTEMS", filed on Jun. 23, 2020, (y) U.S. patent application Ser. No. 16/909,940, entitled "METHOD, APPARATUS, AND SYSTEM FOR QUALIFIED WIRELESS SENSING", filed on Jun. 23, 2020, (z) U.S. patent application Ser. No. 16/945,827, entitled "METHOD, APPARATUS, AND SYSTEM FOR PROCESSING AND PRESENTING LIFE LOG BASED ON A WIRELESS SIGNAL", filed on Aug. 1, 2020, (aa) U.S. patent application Ser. No. 16/945,837, entitled "METHOD, APPARATUS, AND SYSTEM FOR WIRELESS SLEEP MONITORING", filed on Aug. 1, 2020.

TECHNICAL FIELD

The present teaching generally relates to wireless monitoring and tracking. More specifically, the present teaching relates to automatic and adaptive multi-mode wireless monitoring based on wireless channel information.

BACKGROUND

Wireless sensing and tracking has received a lot of attention in the era of Internet of Things. In order to improve the efficiency of device computation, power management, and environmental channel traffic (such as channel availability and usage) management and improve the sensitivity and resolution for events to be detected, an automatic and adaptive multi-mode operation is desirable but not available yet.

SUMMARY

The present teaching generally relates to wireless monitoring and tracking. More specifically, the present teaching relates to automatic and adaptive multi-mode wireless monitoring based on wireless channel information.

In one embodiment, a method implemented by a wireless monitoring system having a processor, a memory communicatively coupled with the processor, and a set of instructions stored in the memory to be executed by the processor, is described. The method comprises: transmitting, using a transmitter, a wireless signal through a wireless multipath channel of a venue; receiving, using a receiver, the wireless signal through the wireless multipath channel, wherein the wireless signal is impacted by the wireless multipath channel and a modulation of an object undergoing a motion in the venue; obtaining a set of channel information (CI) of the wireless multipath channel based on the wireless signal; performing a monitoring task by monitoring the object and the motion of the object based on the set of CI; determining a plurality of admissible system states of the wireless monitoring system, wherein each of the admissible system states is associated with a respective setting of at least one of: the wireless signal, a series of sounding signals in the wireless signal, or the monitoring task; choosing one of the admissible system states to be a system state of the wireless monitoring system based on the monitoring task; and configuring the wireless monitoring system by applying a setting associated with the chosen admissible system state to the wireless monitoring system.

In another embodiment, a method for configuring a wireless monitoring system is described. The method comprises: transmitting, from a transmitter, a wireless signal through a wireless multipath channel of a venue; receiving, by a receiver, the wireless signal through the wireless multipath channel, wherein the wireless signal is impacted by the wireless multipath channel and a modulation of an object undergoing a motion in the venue; obtaining a set of channel information (CI) of the wireless multipath channel based on the wireless signal using a processor, a memory and a set of instructions; performing a monitoring task by monitoring the object and the motion of the object based on the set of CI; determining a plurality of admissible system states of the wireless monitoring system, wherein each of the admissible system states is associated with a respective setting; choosing one of the admissible system states to be a system state of the wireless monitoring system automatically based on the monitoring task; and configuring the wireless monitoring system by applying, based on the system state, the setting associated with the chosen admissible system state to at least one of: the transmitter, the receiver, the wireless signal, a series of sounding signals in the wireless signal, or the set of CI.

In yet another embodiment, a wireless monitoring system is described. The wireless monitoring system comprises: a transmitter, a receiver and a processor. The transmitter is configured for transmitting a wireless signal through a wireless multipath channel of a venue. The receiver is configured for: receiving the wireless signal through the wireless multipath channel, wherein the wireless signal is impacted by the wireless multipath channel and a modulation of an object undergoing a motion in the venue, obtaining a set of channel information (CI) of the wireless multipath channel based on the wireless signal, and performing a monitoring task by monitoring the object and the motion of the object based on the set of CI. The processor is configured for: determining a plurality of admissible system states of the wireless monitoring system, wherein each of the admissible system states is associated with a respective setting of at least one of: the wireless signal, a series of sounding signals in the wireless signal, or the monitoring task, choosing one of the admissible system states to be a system state of the wireless monitoring system based on the monitoring task, and configuring the wireless monitoring system by applying, based on the system state, a setting associated with the chosen admissible system state to at least one of: the transmitter, the receiver, the wireless signal, the set of CI, or the monitoring of the object.

In a different embodiment, a wireless device of a wireless monitoring system is described. The wireless device comprises: a receiver configured to receive a wireless signal transmitted by a transmitter through a wireless multipath channel of a venue, wherein the wireless signal is impacted by the wireless multipath channel and a modulation of an object undergoing a motion in the venue; a processor communicatively coupled with the receiver; a memory communicatively coupled with the processor; and a set of instructions stored in the memory. The set of instructions, when executed by the processor, causes the processor to: obtain a set of channel information (CI) of the wireless multipath channel based on the wireless signal, and perform a monitoring task by monitoring the object and the motion of the object based on the set of CI. A plurality of admissible system states is determined for the wireless monitoring system, wherein each of the admissible system states is associated with a respective setting of at least one of: the wireless signal, a series of sounding signals in the wireless signal, or the monitoring task. One of the admissible system states is chosen to be a system state of the wireless monitoring system based on the monitoring task. The wireless monitoring system is configured by applying, based on the system state, a setting associated with the chosen admissible system state to at least one of: the transmitter, the receiver, the wireless signal, the set of CI, or the monitoring of the object.

Other concepts relate to software for implementing the present teaching on wireless monitoring and tracking. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1:
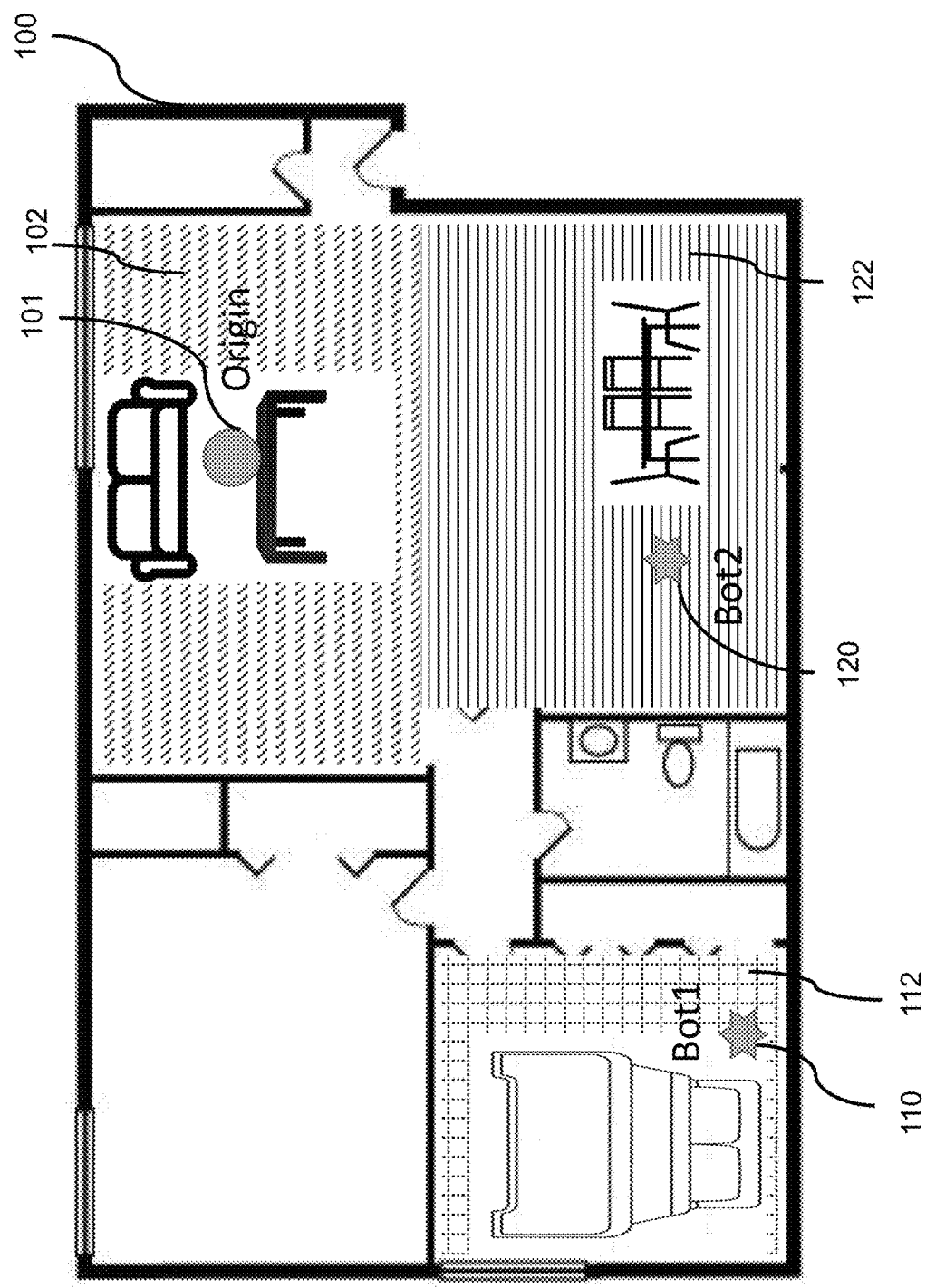
FIG. 1 illustrates an exemplary scenario where object motion is monitored and tracked, according to some embodiments of the present disclosure.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTE/5G/6G/7G/8G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/ 27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise more than one channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/settings/control signal/command/instruction/notification/broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/wireless sensor device, wireless communication device, wireless-enabled device, standard compliant device, and/or receiver. The Type 1 (or Type 2) device may be heterogeneous because, when there are more than one instances of Type 1 (or Type 2) device, they may have different circuitry, enclosure, structure, purpose, auxiliary functionality, chip/IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type 2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI. The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a retraining, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/system, a processor (e.g. logic unit), a memory communicatively coupled with the processor, and a set of instructions stored in the memory to be executed by the processor. Some processors, memories and sets of instructions may be coordinated. There may be multiple Type 1 devices interacting (e.g. communicating, exchange signal/control/notification/other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/Type 2 devices may operate independently and/or collaboratively. A Type 1 and/or Type 2 device may have/comprise/be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied over time. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type 1 and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/7G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/or another wireless transmitter may be associated with at least one processor, memory communicatively coupled with respective processor, and/or respective set of instructions stored in the memory which when executed cause the processor to perform any and/or all steps needed to determine the STI (e.g. motion information), initial STI, initial time, direction, instantaneous location, instantaneous angle, and/or speed, of the object. The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for more than one Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals. For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address. A location of a Type 2 device in the venue may be computed based on the particular MAC address, the series of probe signals, and/or the at least one TSCI obtained by the Type 2 device from the probe signals. The computing may be performed by the Type 2 device. The particular MAC address may be changed (e.g. adjusted, varied, modified) over time. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel. The selected channel may be changed (e.g. adjusted, varied, modified) over time. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger more than one Type 1 devices to broadcast. The triggering may be sequential, partially sequential, partially parallel, or fully parallel. The another device may have more than one wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different. The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same. The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time. The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network/wired network/wireless network/ mesh network/mobile network/cloud. They may share a common memory, or be associated with a common user, user device, profile, account, identity (ID), identifier, household, house, physical address, location, geographic coordinate, IP subnet, SSID, home device, office device, and/or manufacturing device. Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device. The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver). Initially, the Type 1 device may be signal source of a set of initial respective Type 2 devices (i.e. the Type 1 device sends a respective signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 80%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source. If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. 0.01 s for 100 Hz), but each probe signal may experience small time perturbation, perhaps due to timing requirement, timing control, network control, handshaking, message passing, collision avoidance, carrier sensing, congestion, availability of resources, and/or another consideration. The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually. The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc. The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE. The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "Star-Bud hotspot" network).

In one embodiment, a wireless monitoring system may comprise training a classifier of multiple events in a venue based on training TSCI associated with the multiple events. A CI or TSCI associated with an event may be considered/ may comprise a wireless sample/characteristics/fingerprint associated with the event (and/or the venue, the environment, the object, the motion of the object, a state/emotional state/mental state/condition/stage/gesture/gait/action/movement/activity/daily activity/history/event of the object, etc.). For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event. At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/locations/movements/activities. Labels/tags may be generated for the clusters. The clusters may be stored and retrieved. The classifier may be applied to associate the current TSCI (or characteristics/STI or the other analytics/output response, perhaps associated with a current event) with: a cluster, a known/specific event, a class/category/group/grouping/list/cluster/set of known events/subjects/locations/movements/activities, an unknown event, a class/category/group/grouping/list/cluster/set of unknown events/subjects/locations/movements/activities, and/or another event/subject/location/movement/activity/class/category/group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type 2 device (or their locations) may be a permutation of the at least one first Type 2 device (or their locations). A particular second Type 2 device and a particular first Type 2 device may be the same device. A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed (e.g. adjusted, varied, modified) over time; T2 may be updated periodically; T2 may be the beginning of a time period and T1 may be a sliding time in the time period), and (4) a fourth function of the item at time T1 and another item.

At least one of: the first function, the second function, the third function, and/or the fourth function may be a function (e.g. F(X, Y, ...))) with at least two arguments: X and Y. The two arguments may be scalars. The function (e.g. F) may be a function of at least one of: X, Y, (X−Y), (Y−X), abs(X−Y), $X\hat{}a$, $Y\hat{}b$, abs($X\hat{}a−Y\hat{}b$), $(X−Y)\hat{}a$, (X/Y), (X+a)/(Y+b), ($X\hat{}a/Y\hat{}b$), and $((X/Y)\hat{}a−b)$, wherein a and b are may be some predetermined quantities. For example, the function may simply be abs(X−Y), or $(X−Y)\hat{}2$, $(X−Y)\hat{}4$. The function may be a robust function. For example, the function may be $(X−Y)\hat{}2$ when abs (X−Y) is less than a threshold T, and (X−Y)+a when abs(X−Y) is larger than T. Alternatively, the function may be a constant when abs(X−Y) is larger than T. The function may also be bounded by a slowly increasing function when abs(X−y) is larger than T, so that outliers cannot severely affect the result. Another example of the function may be (abs(X/Y)−a), where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that X=(x_1, x_2, ..., x_n) and Y=(y_1, y_2, ..., y_n). The function may be a function of at least one of: x_i, y_i, (x_i−y_i), (y_i−x_i), abs(x_i−y_i), x_i Aa, y_i abs($x\_i\hat{}a−y\_i\hat{}b$), $(x\_i−y\_i)\hat{}a$, (x_i/y_i), (x_i+a)/(y_i+b), $(x\_i−a/y\_i\hat{}b)$, and $((x\_i/y\_i)\hat{}a−b)$, wherein i is a component index of the n-tuple X and Y, and 1<=i<=n. E.g. component index of x_1 is i=1, component index of x_2 is i=2. The function may comprise a component-by-component summation of another function of at least one of the following: x_i, y_i, (x_i−y_i), (y_i−x_i), abs(x_i−y_i), $x\_i\hat{}a$, $y\_i\hat{}b$, abs($x\_i\hat{}a−y\_i\hat{}b$), $(x\_i−y\_i\hat{})\hat{}a$, (x_i/y_i), (x_i+a)/(y_i+b), $(x\_i\hat{}a/y\_i\hat{}b)$, and $((x\_i/y\_i)\hat{}a−b)$, wherein i is the component index of the n-tuple X and Y. For example, the function may be in a form of sum_{i=1}^n (abs(x_i/y_i)−1)/n, or sum {i=1}^n w_i* (abs(x_i/y_i)−1), where w_i is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the i^{th} domain item is mapped to the j^{th} range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising more than one links may be established between first items of the first TSCI and second items of the second TSCI. With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, ...), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated. The first section of the first time duration of the first TSCI may be a sliding section of the first TSCI. The second section of the second time duration of the second TSCI may be a sliding section of the second TSCI. A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in more than one sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%). In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier. The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise more than one projected components. The projection may comprise at least one most significant projected component. The projection may comprise at least one projected component that may be beneficial for the classifier.

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information, transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CSI can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed/processed/monitored in the task.

The channel information may also be modem parameters (e.g. stored or freshly computed) used to process the wireless signal. The wireless signal may comprise a plurality of probe signals. The same modem parameters may be used to process more than one probe signals. The same modem parameters may also be used to process more than one wireless signals. The modem parameters may comprise parameters that indicate settings or an overall configuration for the operation of a radio subsystem or a baseband subsystem of a wireless sensor device (or both). The modem parameters may include one or more of: a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CIC (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CI, change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, L_1 norm, L_2 norm, L_k norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/disclosed/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/supermarket, non-object, absence of an object, presence of an object, object with form, object with changing form, object with no form, mass of fluid, mass of liquid, mass of gas/smoke, fire, flame, electromagnetic (EM) source, EM medium, and/or another object. The object itself may be communicatively coupled with some network, such as WiFi, MiFi, 3G/4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, roof top, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable device may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/, garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/bucket/container, smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car). The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of: a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of: the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, sub-surface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or any Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of: general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11g, 802.11n, 802.11ac, 802.11ad, 802.11af, 802,11ah, 802.11ax, 802.11ay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multi-processor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, post-processing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc. Machine learning, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects. The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type 1 heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, n^th local extremum with positive time offset, local extremum with negative time offset, first local extremum with negative time offset, n^th local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, n^th zero crossing with positive time offset, zero crossing with negative time offset, n^th zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of: an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time. For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition). The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/STI/size/property/trait/habit/behavior, the venue, feature/fixture/furniture/barrier/material/machine/living thing/thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function. The regression analysis may minimize at least one of: error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight.), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost. The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.). The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be disclosed visually and/or described verbally (e.g. using pre-recorded voice, or voice synthesis). The information may be described in text. The information may also be disclosed in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUI), smart speaker, device with voice/audio/speaker capability, virtual reality (VR) device, augmented reality (AR) device, smart car, display in the car, voice assistant, voice assistant in a car, etc. The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model. The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/ stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/ areas may be disclosed in a map/model. Different regions may be color-coded. Different regions may be disclosed with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Wash. Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away. Sometime later, Stephen is convinced that the disclosed wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of: monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface (UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTE/5G/6G/7G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

Type 1 device (transmitter, or Tx) and Type 2 device (receiver, or Rx) may be on same device (e.g. RF chip/IC) or simply the same device. The devices may operate at high frequency band, such as 28 GHz, 60 GHz, 77 GHz, etc. The RF chip may have dedicated Tx antennas (e.g. 32 antennas) and dedicated Rx antennas (e.g. another 32 antennas).

One Tx antenna may transmit a wireless signal (e.g. a series of probe signal, perhaps at 100 Hz). Alternatively, all Tx antennas may be used to transmit the wireless signal with beamforming (in Tx), such that the wireless signal is focused in certain direction (e.g. for energy efficiency or boosting the signal to noise ratio in that direction, or low power operation when "scanning" that direction, or low power operation if object is known to be in that direction).

The wireless signal hits an object (e.g. a living human lying on a bed 4 feet away from the Tx/Rx antennas, with breathing and heart beat) in a venue (e.g. a room). The object motion (e.g. lung movement according to breathing rate, or blood-vessel movement according to heart beat) may impact/modulate the wireless signal. All Rx antennas may be used to receive the wireless signal.

Beamforming (in Rx and/or Tx) may be applied (digitally) to "scan" different directions. Many directions can be scanned or monitored simultaneously. With beamforming, "sectors" (e.g. directions, orientations, bearings, zones, regions, segments) may be defined related to the Type 2 device (e.g. relative to center location of antenna array). For each probe signal (e.g. a pulse, an ACK, a control packet, etc.), a channel information or CI (e.g. channel impulse response/CIR, CSI, CFR) is obtained/computed for each sector (e.g. from the RF chip). In breathing detection, one may collect CIR in a sliding window (e.g. 30 sec, and with 100 Hz sounding/probing rate, one may have 3000 CIR over 30 sec).

The CIR may have many taps (e.g. N1 components/taps). Each tap may be associated with a time lag, or a time-of-flight (tof, e.g. time to hit the human 4 feet away and back). When a person is breathing in a certain direction at a certain distance (e.g. 4 ft), one may search for the CIR in the "certain direction". Then one may search for the tap corresponding to the "certain distance". Then one may compute the breathing rate and heart rate from that tap of that CIR.

One may consider each tap in the sliding window (e.g. 30 second window of "component time series") as a time function (e.g. a "tap function", the "component time series"). One may examine each tap function in search of a strong periodic behavior (e.g. corresponds to breathing, perhaps in the range of 10 bpm to 40 bpm).

The Type 1 device and/or the Type 2 device may have external connections/links and/or internal connections/links. The external connections (e.g. connection 1110) may be associated with 2G/2.5G/3G/3.5G/4G/LTE/5G/6G/7G/NBIoT, UWB, WiMax, Zigbee, 802.16 etc. The internal connections (e.g., 1114A and 1114B, 1116, 1118, 1120) may be associated with WiFi, an IEEE 802.11 standard, 802.11a/b/g/n/ac/ad/af/ag/ah/ai/aj/aq/ax/ay, Bluetooth, Bluetooth 1.0/1.1/1.2/2.0/2.1/3.0/4.0/4.1/4.2/5, BLE, mesh network, an IEEE 802.16/1/1 a/1b/2/2a/a/b/c/d/e/f/g/h/i/j/k/l/m/n/o/p/ standard.

The Type 1 device and/or Type 2 device may be powered by battery (e.g. AA battery, AAA battery, coin cell battery, button cell battery, miniature battery, bank of batteries, power bank, car battery, hybrid battery, vehicle battery, container battery, non-rechargeable battery, rechargeable battery, NiCd battery, NiMH battery, Lithium ion battery, Zinc carbon battery, Zinc chloride battery, lead acid battery, alkaline battery, battery with wireless charger, smart battery, solar battery, boat battery, plane battery, other battery, temporary energy storage device, capacitor, fly wheel).

Any device may be powered by DC or direct current (e.g. from battery as described above, power generator, power convertor, solar panel, rectifier, DC-DC converter, with various voltages such as 1.2V, 1.5V, 3V, 5V, 6V, 9V, 12V, 24V, 40V, 42V, 48V, 110V, 220V, 380V, etc.) and may thus have a DC connector or a connector with at least one pin for DC power.

Any device may be powered by AC or alternating current (e.g. wall socket in a home, transformer, invertor, shore-power, with various voltages such as 100V, 110V, 120V, 100-127V, 200V, 220V, 230V, 240V, 220-240V, 100-240V, 250V, 380V, 50 Hz, 60 Hz, etc.) and thus may have an AC connector or a connector with at least one pin for AC power. The Type 1 device and/or the Type 2 device may be positioned (e.g. installed, placed, moved to) in the venue or outside the venue.

For example, in a vehicle (e.g. a car, truck, lorry, bus, special vehicle, tractor, digger, excavator, teleporter, bulldozer, crane, forklift, electric trolley, AGV, emergency vehicle, freight, wagon, trailer, container, boat, ferry, ship, submersible, airplane, air-ship, lift, mono-rail, train, tram, rail-vehicle, railcar, etc.), the Type 1 device and/or Type 2 device may be an embedded device embedded in the vehicle, or an add-on device (e.g. aftermarket device) plugged into a port in the vehicle (e.g. OBD port/socket, USB port/socket, accessory port/socket, 12V auxiliary power outlet, and/or 12V cigarette lighter port/socket).

For example, one device (e.g. Type 2 device) may be plugged into 12V cigarette lighter/accessory port or OBD port or the USB port (e.g. of a car/truck/vehicle) while the other device (e.g. Type 1 device) may be plugged into 12V cigarette lighter/accessory port or the OBD port or the USB port. The OBD port and/or USB port can provide power, signaling and/or network (of the car/truck/vehicle). The two devices may jointly monitor the passengers including children/babies in the car. They may be used to count the passengers, recognize the driver, detect presence of passenger in a particular seat/position in the vehicle.

In another example, one device may be plugged into 12V cigarette lighter/accessory port or OBD port or the USB port of a car/truck/vehicle while the other device may be plugged into 12V cigarette lighter/accessory port or OBD port or the USB port of another car/truck/vehicle.

In another example, there may be many devices of the same type A (e.g. Type 1 or Type 2) in many heterogeneous vehicles/portable devices/smart gadgets (e.g. automated guided vehicle/AGV, shopping/luggage/moving cart, parking ticket, golf cart, bicycle, smart phone, tablet, camera, recording device, smart watch, roller skate, shoes, jackets, goggle, hat, eye-wear, wearable, Segway, scooter, luggage tag, cleaning machine, vacuum cleaner, pet tag/collar/wearable/implant), each device either plugged into 12V accessory port/OBD port/USB port of a vehicle or embedded in a vehicle. There may be one or more device of the other type B (e.g. B is Type 1 if A is Type 2, or B is Type 2 if A is Type 1) installed at locations such as gas stations, street lamp post, street corners, tunnels, multi-storey parking facility, scattered locations to cover a big area such as factory/stadium/train station/shopping mall/construction site. The Type A device may be located, tracked or monitored based on the TSCI.

The area/venue may have no local connectivity, e.g., broadband services, WiFi, etc. The Type 1 and/or Type 2 device may be portable. The Type 1 and/or Type 2 device may support plug and play.

Pairwise wireless links may be established between many pairs of devices, forming the tree structure. In each pair (and the associated link), a device (second device) may be a non-leaf (Type B). The other device (first device) may be a leaf (Type A or Type B) or non-leaf (Type B). In the link, the first device functions as a Bot (Type 1 device or a Tx device) to send a wireless signal (e.g. probe signal) through the wireless multipath channel to the second device. The second device may function as an Origin (Type 2 device or Rx device) to receive the wireless signal, obtain the TSCI and compute a "linkwise analytics" based on the TSCI.

FIG. 1 illustrates an exemplary scenario where object motion is detected based on channel state information in a venue, according to one embodiment of the present teaching.

For example, as shown in FIG. 1, in a 2-bedroom apartment 100, Origin 101 may be placed in the living-room area 102, Bot 1 110 may be placed in a bedroom1-area 112, and Bot 2 120 may be placed in the dining-room area 122. Each of Bot 1 110 and Bot 2 120 can transmit a wireless signal to the Origin 101, which can obtain channel information of a wireless multipath channel based on the wireless signal. The Origin 101, by itself or through a third device like a motion detector, can compute motion information based on the channel information and detect object motion/activity based on the motion information. That is, the Origin 101, by itself or through a third device like a motion detector, can detect object motion/activity based on wireless signals transmitted by Bot 1 110 and/or Bot 2 120.

If object motion/activity is detected based on wireless signals transmitted by both Bot 1 110 and Bot 2 120, the activity/motion or the object (e.g. person/user) may be in the living-room area 102. If object motion/activity is detected based only on wireless signals transmitted by Bot 1 110, the activity/motion or the object (e.g. person/user) may be in the bedroom-1 area 112. If object motion/activity is detected based only on wireless signals transmitted by Bot 2 120, the activity/motion or the object (e.g. person/user) may be in the dining-room area 122. If object motion/activity cannot be detected based on wireless signals transmitted by either Bot 1 110 or Bot 2 120, then it may be determined that nobody and no object is in the apartment 100. The corresponding area where the activity/motion/person/user is detected may be marked with a predetermined pattern.

Figure 2A:
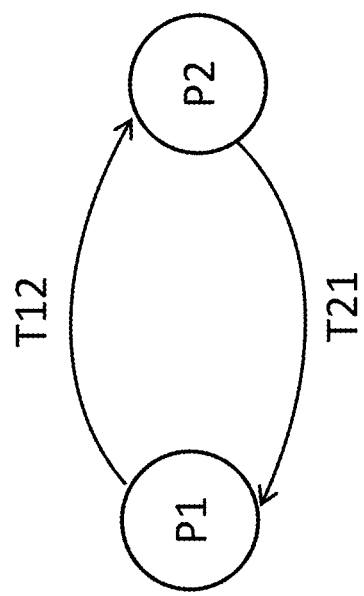
FIG. 2A illustrates a mode transition process of a wireless monitoring system, according to some embodiments of the present disclosure.
Figure 2B:
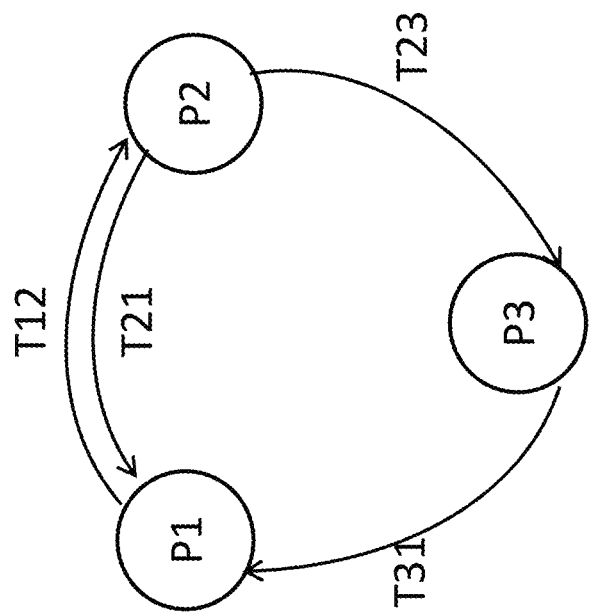
FIG. 2B illustrates another mode transition process of a wireless monitoring system, according to some embodiments of the present disclosure.

A wireless monitoring system including Bot(s) and Origin(s) may enter different operation modes, e.g. an inactive mode, hibernation mode, sleep mode, stand-by mode, low-power mode, OFF mode and/or power-down mode. Exemplary transitions between the system operation modes are shown in FIG. 2A and FIG. 2B. As shown in FIG. 2A, a system may first operate on mode 1 with a parameter P1. Upon some triggering event T12, the system may transit to operation mode 2 with parameter P2. Then, upon another triggering event T21, the system may transit back to operation mode 1. As shown in FIG. 2B, there may exist another operation mode 3 with a parameter P3. In one embodiment, a system operates currently on mode 2. Upon some triggering event T23, the system may transit to operation mode 3. Then, upon another triggering event T31, the system may transit back to operation mode 1.

Figure 3:
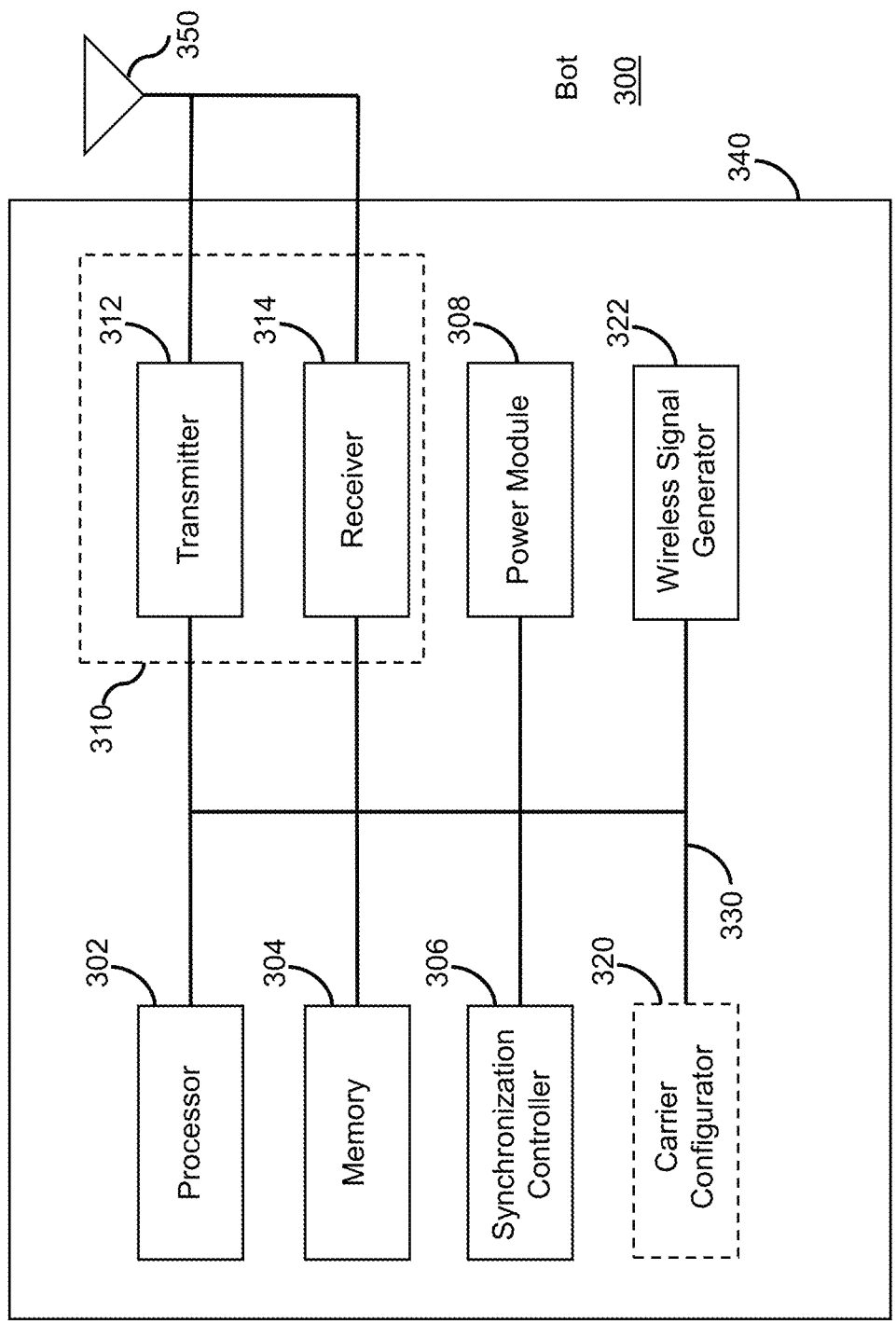
FIG. 3 illustrates an exemplary block diagram of a first wireless device of a wireless monitoring system, according to one embodiment of the present teaching.

FIG. 3 illustrates an exemplary block diagram of a first wireless device, e.g. a Bot 300, of a wireless monitoring system, according to one embodiment of the present teaching. The Bot 300 is an example of a device that can be configured to implement the various methods described herein. As shown in FIG. 3, the Bot 300 includes a housing 340 containing a processor 302, a memory 304, a transceiver 310 comprising a transmitter 312 and receiver 314, a synchronization controller 306, a power module 308, an optional carrier configurator 320 and a wireless signal generator 322.

In this embodiment, the processor 302 controls the general operation of the Bot 300 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 304, which can include both read-only memory (ROM) and random access memory (RAM), can provide instructions and data to the processor 302. A portion of the memory 304 can also include non-volatile random access memory (NVRAM). The processor 302 typically performs logical and arithmetic operations based on program instructions stored within the memory 304. The instructions (a.k.a., software) stored in the memory 304 can be executed by the processor 302 to perform the methods described herein. The processor 302 and the memory 304 together form a processing system that stores and executes software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

The transceiver 310, which includes the transmitter 312 and receiver 314, allows the Bot 300 to transmit and receive data to and from a remote device (e.g., an Origin or another Bot). An antenna 350 is typically attached to the housing 340 and electrically coupled to the transceiver 310. In various embodiments, the Bot 300 includes (not shown) multiple transmitters, multiple receivers, and multiple transceivers. In one embodiment, the antenna 350 is replaced with a multi-antenna array 350 that can form a plurality of beams each of which points in a distinct direction. The transmitter 312 can be configured to wirelessly transmit signals having different types or functions, such signals being generated by the processor 302. Similarly, the receiver 314 is configured to receive wireless signals having different types or functions, and the processor 302 is configured to process signals of a plurality of different types.

The Bot 300 in this example may serve as Bot 1 110 or Bot 2 120 in FIG. 1 for detecting object motion in a venue. For example, the wireless signal generator 322 may generate and transmit, via the transmitter 312, a wireless signal through a wireless multipath channel impacted by a motion of an object in the venue. The wireless signal carries information of the channel. Because the channel was impacted by the motion, the channel information includes motion information that can represent the motion of the object. As such, the motion can be indicated and detected based on the wireless signal. The generation of the wireless signal at the wireless signal generator 322 may be based on a request for motion detection from another device, e.g. an Origin, or based on a system pre-configuration. That is, the Bot 300 may or may not know that the wireless signal transmitted will be used to detect motion.

The synchronization controller 306 in this example may be configured to control the operations of the Bot 300 to be synchronized or un-synchronized with another device, e.g. an Origin or another Bot. In one embodiment, the synchronization controller 306 may control the Bot 300 to be synchronized with an Origin that receives the wireless signal transmitted by the Bot 300. In another embodiment, the synchronization controller 306 may control the Bot 300 to transmit the wireless signal asynchronously with other Bots. In another embodiment, each of the Bot 300 and other Bots may transmit the wireless signals individually and asynchronously.

The carrier configurator 320 is an optional component in Bot 300 to configure transmission resources, e.g. time and carrier, for transmitting the wireless signal generated by the wireless signal generator 322. In one embodiment, each CI of the time series of CI has one or more components each corresponding to a carrier or sub-carrier of the transmission of the wireless signal. The detection of the motion may be based on motion detections on any one or any combination of the components.

The power module 308 can include a power source such as one or more batteries, and a power regulator, to provide regulated power to each of the above-described modules in FIG. 3. In some embodiments, if the Bot 300 is coupled to a dedicated external power source (e.g., a wall electrical outlet), the power module 308 can include a transformer and a power regulator.

The various modules discussed above are coupled together by a bus system 330. The bus system 330 can include a data bus and, for example, a power bus, a control signal bus, and/or a status signal bus in addition to the data bus. It is understood that the modules of the Bot 300 can be operatively coupled to one another using any suitable techniques and mediums.

Although a number of separate modules or components are illustrated in FIG. 3, persons of ordinary skill in the art will understand that one or more of the modules can be combined or commonly implemented. For example, the processor 302 can implement not only the functionality described above with respect to the processor 302, but also implement the functionality described above with respect to the wireless signal generator 322. Conversely, each of the modules illustrated in FIG. 3 can be implemented using a plurality of separate components or elements.

Figure 4:
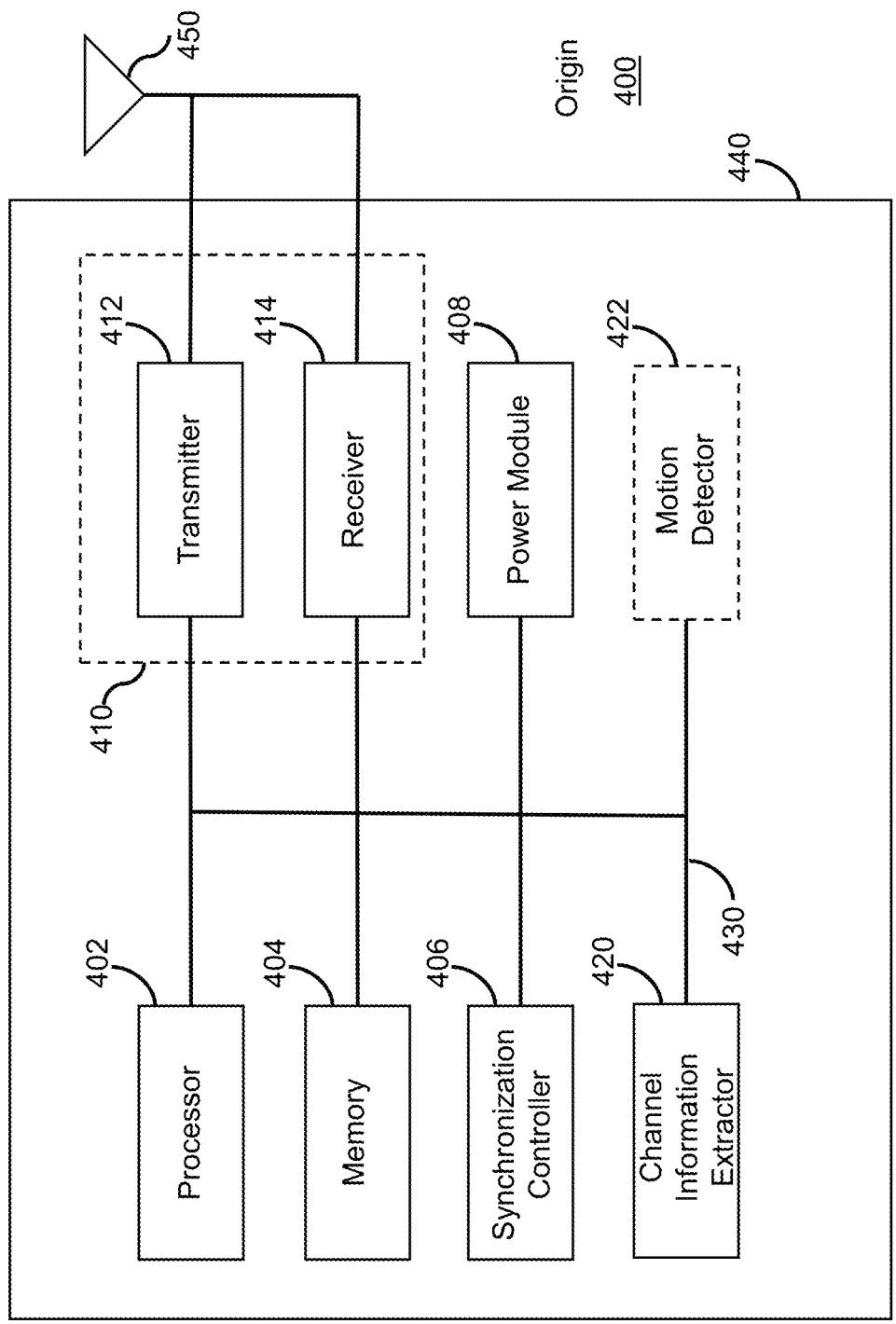
FIG. 4 illustrates an exemplary block diagram of a second wireless device of a wireless monitoring system, according to one embodiment of the present teaching.

FIG. 4 illustrates an exemplary block diagram of a second wireless device, e.g. an Origin 400, of a wireless monitoring system, according to one embodiment of the present teaching. The Origin 400 is an example of a device that can be configured to implement the various methods described herein. The Origin 400 in this example may serve as Origin 101 in FIG. 1 for detecting object motion in a venue. As shown in FIG. 4, the Origin 400 includes a housing 440 containing a processor 402, a memory 404, a transceiver 410 comprising a transmitter 412 and a receiver 414, a power module 408, a synchronization controller 406, a channel information extractor 420, and an optional motion detector 422.

In this embodiment, the processor 402, the memory 404, the transceiver 410 and the power module 408 work similarly to the processor 302, the memory 304, the transceiver 310 and the power module 308 in the Bot 300. An antenna 450 or a multi-antenna array 450 is typically attached to the housing 440 and electrically coupled to the transceiver 410.

The Origin 400 may be a second wireless device that has a different type from that of the first wireless device (e.g. the Bot 300). In particular, the channel information extractor 420 in the Origin 400 is configured for receiving the wireless signal through the wireless multipath channel impacted by the motion of the object in the venue, and obtaining a time series of channel information (CI) of the wireless multipath channel based on the wireless signal. The channel information extractor 420 may send the extracted CI to the optional motion detector 422 or to a motion detector outside the Origin 400 for detecting object motion in the venue.

The motion detector 422 is an optional component in the Origin 400. In one embodiment, it is within the Origin 400 as shown in FIG. 4. In another embodiment, it is outside the Origin 400 and in another device, which may be a Bot, another Origin, a cloud server, a fog server, a local server, and an edge server. The optional motion detector 422 may be configured for detecting the motion of the object in the venue based on motion information related to the motion of the object. The motion information associated with the first and second wireless devices is computed based on the time series of CI by the motion detector 422 or another motion detector outside the Origin 400.

The synchronization controller 406 in this example may be configured to control the operations of the Origin 400 to be synchronized or un-synchronized with another device, e.g. a Bot, another Origin, or an independent motion detector. In one embodiment, the synchronization controller 406 may control the Origin 400 to be synchronized with a Bot that transmits a wireless signal. In another embodiment, the synchronization controller 406 may control the Origin 400 to receive the wireless signal asynchronously with other Origins. In another embodiment, each of the Origin 400 and other Origins may receive the wireless signals individually and asynchronously. In one embodiment, the optional motion detector 422 or a motion detector outside the Origin 400 is configured for asynchronously computing respective heterogeneous motion information related to the motion of the object based on the respective time series of CI.

The various modules discussed above are coupled together by a bus system 430. The bus system 430 can include a data bus and, for example, a power bus, a control signal bus, and/or a status signal bus in addition to the data bus. It is understood that the modules of the Origin 400 can be operatively coupled to one another using any suitable techniques and mediums.

Although a number of separate modules or components are illustrated in FIG. 4, persons of ordinary skill in the art will understand that one or more of the modules can be combined or commonly implemented. For example, the processor 402 can implement not only the functionality described above with respect to the processor 402, but also implement the functionality described above with respect to the channel information extractor 420. Conversely, each of the modules illustrated in FIG. 4 can be implemented using a plurality of separate components or elements.

In one embodiment, in addition to the Bot 300 and the Origin 400, the system may also comprise: a third wireless device, e.g. another Bot, configured for transmitting an additional heterogeneous wireless signal through an additional wireless multipath channel impacted by the motion of the object in the venue, and a fourth wireless device, e.g. another Origin, that has a different type from that of the third wireless device. The fourth wireless device may be configured for: receiving the additional heterogeneous wireless signal through the additional wireless multipath channel impacted by the motion of the object in the venue, and obtaining a time series of additional channel information (CI) of the additional wireless multipath channel based on the additional heterogeneous wireless signal. The additional CI of the additional wireless multipath channel is associated with a different protocol or configuration from that associated with the CI of the wireless multipath channel. For example, the wireless multipath channel is associated with LTE, while the additional wireless multipath channel is associated with Wi-Fi. In this case, the optional motion detector 422 or a motion detector outside the Origin 400 is configured for detecting the motion of the object in the venue based on both the motion information associated with the first and second wireless devices and additional motion information associated with the third and fourth wireless devices computed by at least one of: an additional motion detector and the fourth wireless device based on the time series of additional CI.

Figure 5:
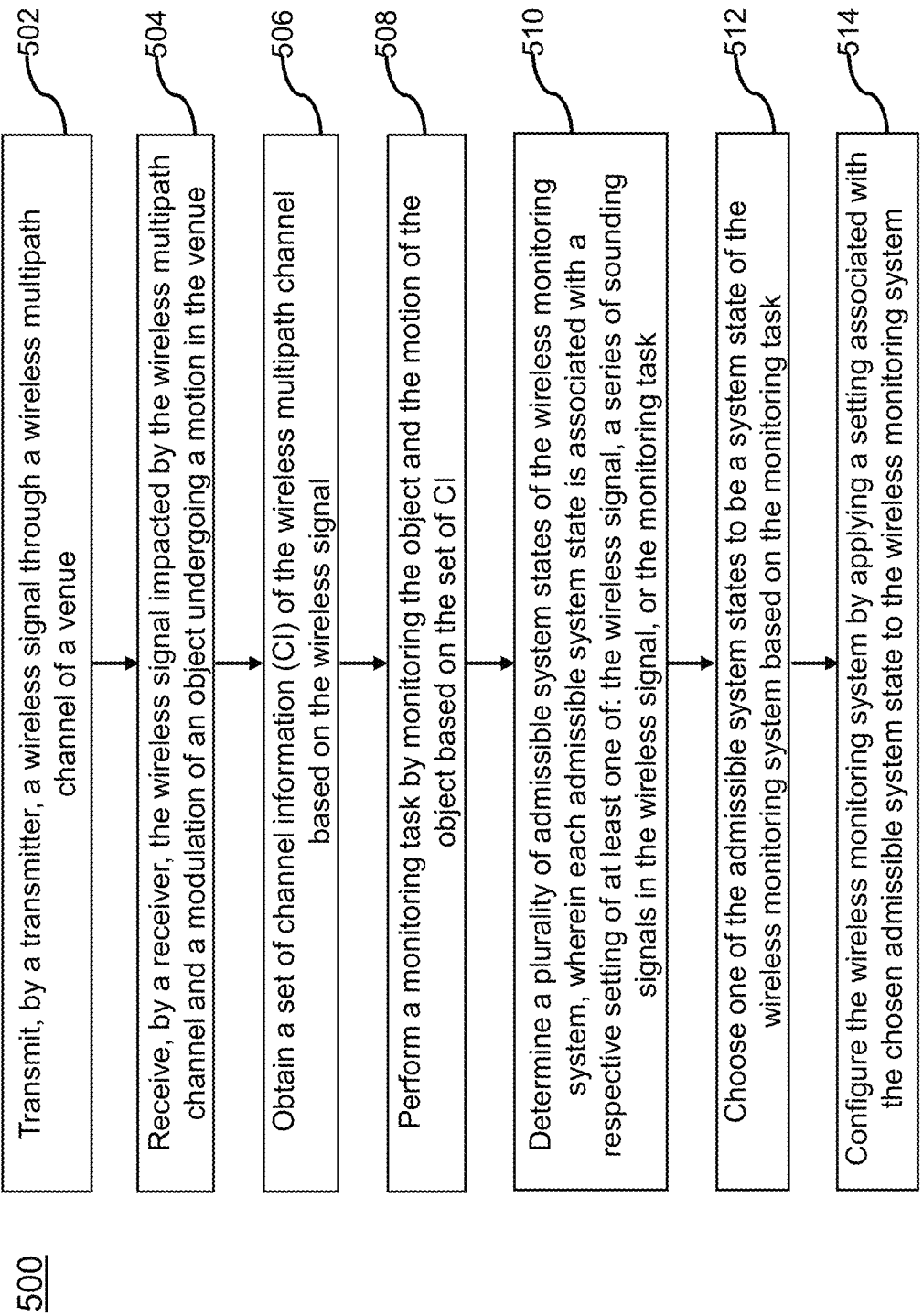
FIG. 5 illustrates a flow chart of an exemplary method of a wireless monitoring system, according to some embodiments of the present teaching.

FIG. 5 illustrates a flow chart of an exemplary method 500 of a wireless monitoring system, according to some embodiments of the present teaching. At operation 502, a transmitter, e.g. on a Bot, transmits a wireless signal through a wireless multipath channel of a venue. At operation 504, a receiver, e.g. on an Origin, receives the wireless signal that is impacted by the wireless multipath channel and a modulation of an object undergoing a motion in the venue. At operation 506, a set of channel information (CI) of the wireless multipath channel is obtained based on the wireless signal. At operation 508, based on the set of CI, a monitoring task is performed to monitor the object and the motion of the object. At operation 510, a plurality of admissible system states of the wireless monitoring system is determined. Each admissible system state is associated with a respective setting of at least one of: the wireless signal, a series of sounding signals in the wireless signal, or the monitoring task. One of the admissible system states is chosen at operation 512 to be a system state of the wireless monitoring system based on the monitoring task. At operation 514, the wireless monitoring system is configured by applying a setting associated with the chosen admissible system state to the wireless monitoring system. The order of the operations in FIG. 5 may be changed according to various embodiments of the present teaching.

Figure 6:
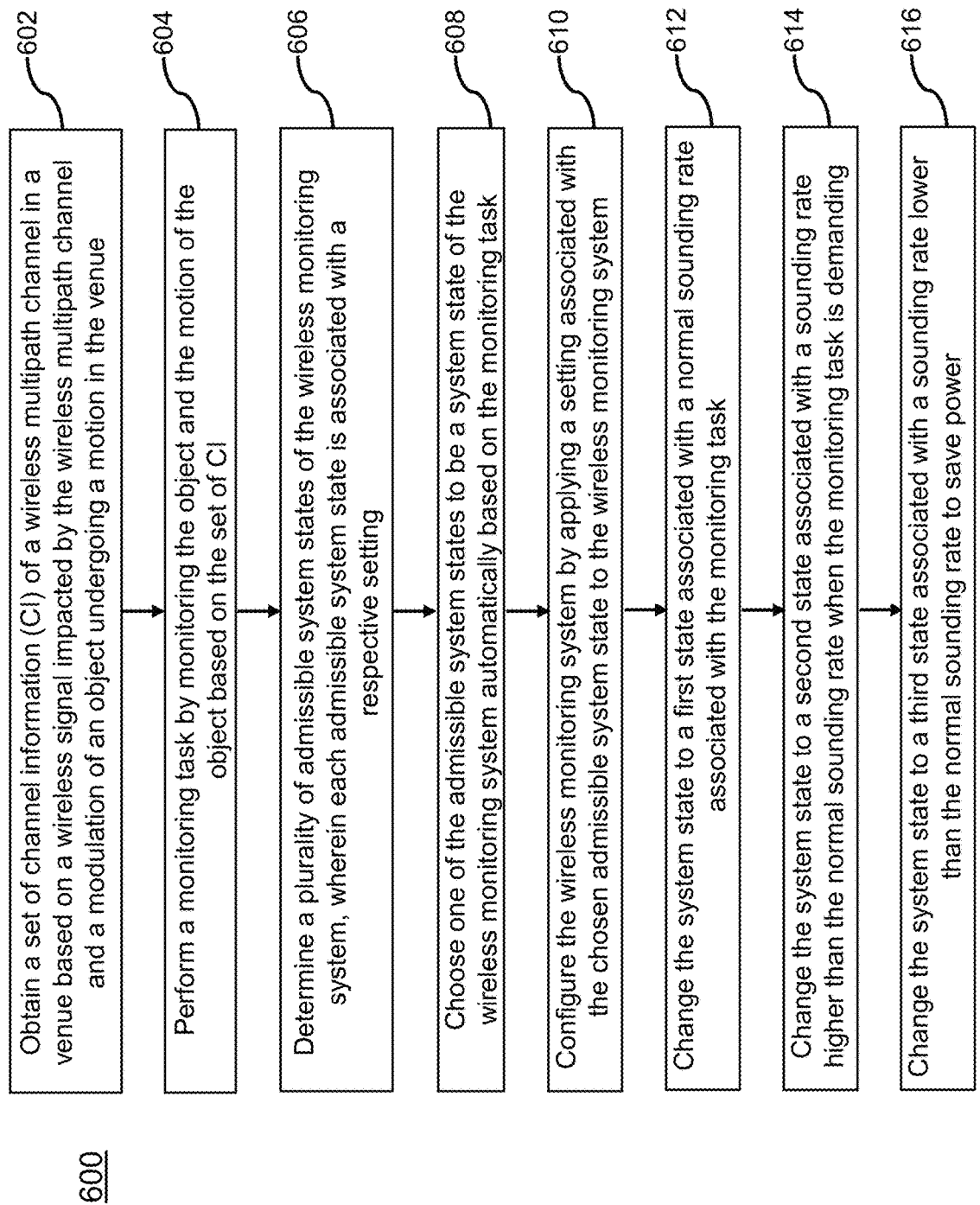
FIG. 6 illustrates a flow chart of another exemplary method of a wireless monitoring system, according to some embodiments of the present teaching.

FIG. 6 illustrates a flow chart of another exemplary method 600 of a wireless monitoring system, according to some embodiments of the present teaching. At operation 602, a set of channel information (CI) of a wireless multipath channel in a venue is obtained based on a wireless signal that is impacted by the wireless multipath channel and a modulation of an object undergoing a motion in the venue. At operation 604, based on the set of CI, a monitoring task is performed to monitor the object and the motion of the object. At operation 606, a plurality of admissible system states of the wireless monitoring system is determined. Each admissible system state is associated with a respective setting. One of the admissible system states is chosen at operation 608 to be a system state of the wireless monitoring system automatically based on the monitoring task. At operation 610, the wireless monitoring system is configured by applying a setting associated with the chosen admissible system state to the wireless monitoring system. Optionally at operation 612, the system state is changed to a first state associated with a normal sounding rate associated with the monitoring task. Optionally at operation 614, the system state is changed to a second state associated with a sounding rate higher than the normal sounding rate when the monitoring task is demanding. Optionally at operation 616, the system state is changed to a third state associated with a sounding rate lower than the normal sounding rate to save power. The order of the operations in FIG. 6 may be changed according to various embodiments of the present teaching.

Humanoid mannequins may mimic human activities as testing subjects for WiFi Sensing. Wireless sensing has brought many benefits to people's daily life. But involving human subject in testing for wireless sensing and monitoring applications may pose potential health risks or inconvenience/dependency, as the test process and the process on regulation may be long and costly. There may also exist liability issues due to potential occupational injury. A duplicable/repeatable/scalable testing process is in great need because they can reduce time for product development and commercialization and create standardized test protocols for wireless sensing industry.

There are examples of using replacement subjects for testing. For example, a Specific Absorption Rate (SAR) testing is the radiofrequency (RF) dosimetry quantification of the magnitude and distribution of absorbed electromagnetic energy within biological objects that are exposed to RF fields.

A Specific Anthropomorphic Mannequin (SAM) is a phantom composed of specific materials that simulate the dielectric properties of human body. The conductivity and permittivity of the human body is mimicked with a liquid solution of, sugar, salt, water and other ingredients. Different compositions of the solution may be used for different frequencies, for example, Wi-Fi or 5G.

From the human body standpoint of view, a SAM can mimic the radio absorption, and that radio absorption dosage can be used to estimate the effect to the body. However, from the wireless sensing standpoint of view, the absorption of a SAM could mimic the actual interaction, given the similar size and shape of human beings or pets, with the radio signals (e.g. WiFi multipath), and potentially could be used as a test subject that replaces a human subject, in the WiFi Sensing testing.

An exemplary approach using replacement subject is described below. First, one can select a radio frequency band of interest, e.g. WiFi 5 GHz band (5.250-5.350 GHz, 5.470-5.725 GHz). Second, the SAM is used for this frequency band. A material RF response can be represented by complex permittivity $\varepsilon_r = \varepsilon'_r + j\varepsilon''_r$. Different sizes of shape may be tested such as human adult, child, infant, pets, etc. They may be stationary, or with movable parts (knee) or active-moving parts that are controlled by robotic means (e.g. a chest movement). In one embodiment, materials (e.g. coating or infill) can be applied to a mannequin for customization. One may utilize a humanoid robot, or robotic parts in some approaches. SAM can be from fashion industry, car industry, or medical industry.

Figure 7:
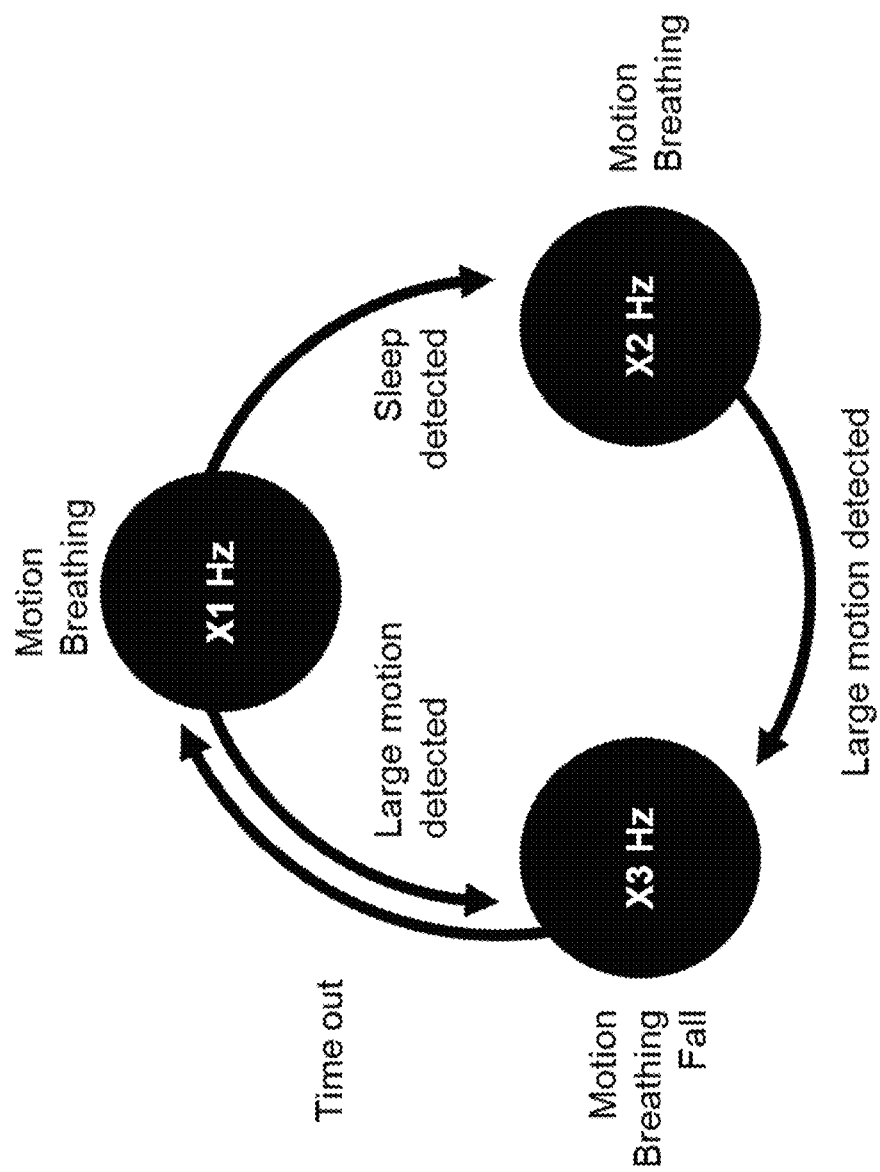
FIG. 7 illustrates a system state transition process of a wireless monitoring system, according to some embodiments of the present disclosure.

A wireless monitoring system may be in any one of a plurality of admissible system states, where each of the admissible system states is associated with a respective setting of at least one of: a wireless signal, a series of sounding signals in the wireless signal, or a monitoring task. At a given time, the system operates in a system state chosen from the admissible system states. For example, FIG. 7 illustrates a system state transition process of a wireless monitoring system, according to some embodiments of the present disclosure. The wireless monitoring system related to FIG. 7 can operate in different system states, where each system state corresponds to sounding signals at a different frequency.

In one embodiment, the wireless monitoring system of FIG. 7 may be utilized to monitor a wellness of a person, e.g. by performing daily activity, sleep monitoring, and/or fall detection. The wireless monitoring system may have a default state with a frequency of X1 Hz sounding signal, to search for motion or breathing activity. This default frequency is chosen to have a good performance, e.g. high enough detection rate, when no one is at home, or in a state where the system is expected to experience in most frequent situations.

When a triggering event happens, the system transfers from one state to another. For example, when a large motion is detected and certain criteria are met, the system changes its sounding signal frequency to X3 Hz to enter another state, where X3>X1. In this new state, the system can standby to detect a fall event, in addition to motion and breathing detection. When certain time-out condition is met, e.g. after a predetermined period without a fall event detection, the system switches back to the default state with X1 Hz sounding signals.

When the system engine is at a sleep stage, the system can either stay at the default X1 Hz state or switch to a X2 Hz state, as shown in FIG. 7, where X2<X1. The X1 Hz state enables the system to perform normal sleep monitoring with X1 Hz sounding signals, where a sleep apnea can only be detected when it lasts for more than a first time period T1. The X2 Hz state enables the system to perform normal sleep monitoring with X2 Hz sounding signals, where a sleep apnea can be detected whenever it lasts for more than a second time period T2, where T2 is shorter than T1. When a large motion or motion pattern is detected (e.g. rolling toward the edge of the bed), the system switches to the X3 Hz state to stand by for fall event from the bed, where X3>X2.

In some embodiments, the system can use the X3 Hz sounding signal as a default and constant frequency, such that no frequency switch happens upon any triggering event. In case a triggering event happens, the system engine may just perform down-sampling and use a X1 Hz component for motion and breathing detection.

Figure 8:
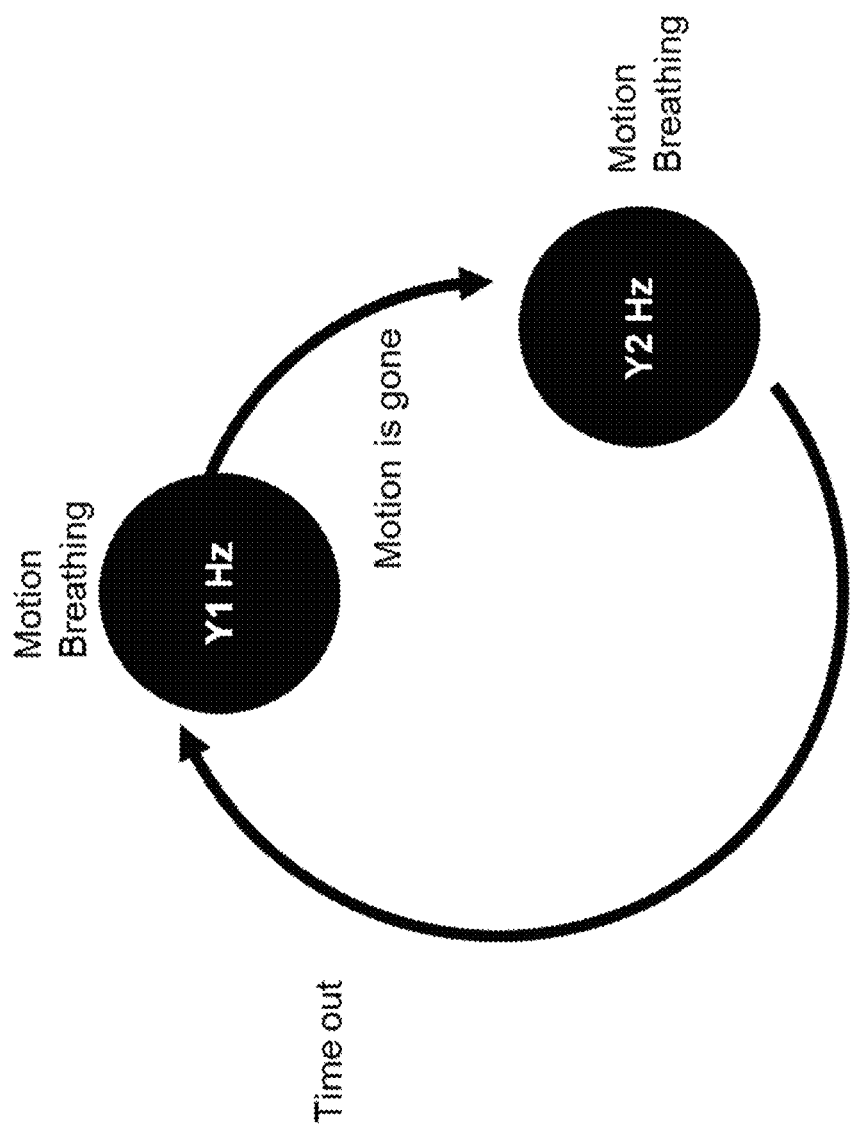
FIG. 8 illustrates another system state transition process of a wireless monitoring system, according to some embodiments of the present disclosure.

FIG. 8 illustrates another system state transition process of a wireless monitoring system, according to some embodiments of the present disclosure. The wireless monitoring system related to FIG. 8 can operate in different system states, where each system state corresponds to sounding signals at a different frequency. In one embodiment, the wireless monitoring system of FIG. 8 may be utilized to detect a presence of an object in a home or space, and/or monitor a motion of the object. For example, the system may be a home monitoring or public space monitoring system, to ensure security.

The system according to FIG. 8 may have a default state with a frequency of Y1 Hz sounding signal, to detect a motion in the space. An alert is sent from the system when a motion is detected. After the motion dies away, the system may stay at the Y1 Hz state for breathing detection or may switch to a Y2 Hz state for finer resolution or shorter no-breathing window, where Y2>Y1. In one embodiment, the Y2 Hz state enables the system to performing wireless monitoring using a Y2 Hz sounding signal, to detect motions in a scenario when an intruder is trying not to move but intends to stay in that space, or when people stay in the mall, museum, or a public restroom after it closes its business of the day. When certain time-out condition is met, e.g. after a predetermined period without motion detection, the system switches back to the default state with Y1 Hz sounding signals.

In other embodiments, a system can be designed to alternate between multiple states, instead of having one single default state. For example, the system of FIG. 8 may stay in the Y1 Hz state for S1 seconds, then switch to the Y2 Hz state for S2 seconds, and then switch back to the Y1 Hz.

The present teaching generally relates to wireless monitoring and tracking. More specifically, the present teaching relates to automatic and adaptive multi-mode wireless monitoring based on wireless channel information. The following numbered clauses provide implementation examples for configuring a wireless monitoring system by selecting and/or setting a system state from a number of admissible system states.

Clause 1. A method of configuring a wireless monitoring system, comprising: transmitting a wireless signal from a Type1 heterogeneous wireless device through a wireless multipath channel of a venue; receiving the wireless signal by a Type2 heterogeneous wireless device through the wireless multipath channel, wherein the received wireless signal differs from the transmitted wireless signal due to the wireless multipath channel of the venue and a modulation of the wireless signal by an object undergoing a motion in the venue; obtaining a set of channel information (CI) of the wireless multipath channel based on the received wireless signal using a processor, a memory and a set of instructions; performing a monitoring task by monitoring the object and the motion of the object based on the set of CI; determining a number of admissible system states of the wireless monitoring system, each admissible system state associated with a respective setting of at least one of: the wireless signal, a signaling in the wireless signal, a series of sounding signals in the wireless signal, a timing of the sounding signals in the wireless signal, a sounding frequency of the sounding signals, a frame type of the wireless signal, a field of the frame type of the wireless signal, a generation of the wireless signal by the Type1 device, a transmission of the wireless signal by the Type1 device, a reception of the wireless signal by the Type2 device, a processing of the wireless signal by the Type2 device, a coordination of the Type1 device and the Type2 device regarding the transmission of the wireless signal, a coordination with other devices regarding the transmission of the wireless signal, the set of CI, the obtaining of the set of CI of the wireless multipath channel based on the received wireless signal, the monitoring task of the object, a customization of the monitoring task, a computation for the monitoring task, a computation for monitoring the object based on the CI; choosing a system state to be one of the admissible system states based on the monitoring task; and configuring the wireless monitoring system by applying a setting associated with the chosen admissible system state to the wireless monitoring system.

Clause 2. The method of configuring the wireless monitoring system of clause 1, further comprising: choosing the system state to be the chosen admissible system state automatically based on at least one of: at least one of: a negotiation, a handshake, or a coordination, between at least two of: the Type1 device, the Type2 device, a server, another Type1 device or another Type2 device, at least one of: a constraint, a requirement and a condition of the monitoring task, at least one of: a command, a request, a coordination, and a planning of a server, a testing procedure, or an optimization criterion.

Clause 3. The method of configuring the wireless monitoring system of clause 1, further comprising: performing a testing procedure associated with the monitoring task; transmitting a testing wireless signal from a testing Type1 heterogeneous wireless device through a testing wireless multipath channel of a testing venue; receiving the testing wireless signal by a testing Type2 heterogeneous wireless device through the testing wireless multipath channel, wherein the received testing wireless signal differs from the transmitted testing wireless signal due to the testing wireless multipath channel of the testing venue and a modulation of the testing wireless signal by a testing object undergoing a testing motion in the testing venue; obtaining a set of testing channel information (CI) of the testing wireless multipath channel based on the received testing wireless signal using a testing processor, a testing memory and a set of testing instructions; performing the testing procedure by monitoring the testing object and the testing motion of the testing object based on the set of testing CI; and choosing the system state to be the chosen admissible system states automatically based on the testing procedure.

Clause 4. The method of configuring the wireless monitoring system of clause 3, further comprising: wherein the testing Type1 device comprises at least one of: the Type1 device, another Type1 device, the Type2 device, another Type2 device and another wireless device; wherein the testing Type2 device comprises at least one of: the Type1 device, another Type1 device, the Type2 device, another Type2 device and another wireless device; wherein the testing venue comprises at least one of: the venue, the venue in a testing condition, the venue in at least one candidate operating condition, the venue in at least one candidate manifestation, the venue in at least one candidate expression, the venue without the object, the venue with at least one of: the object, or a testing object similar to the object, the venue with the object or the testing object in at least one target expression to be monitored in the monitoring task, and the venue with the object or the testing object performing at least one target motion to be monitored in the monitoring task; positioning the testing Type1 device at at least one candidate location in the testing venue, one of the candidate location being location of the Type1 device; positioning the testing Type2 device at at least one candidate location in the testing venue, one of the candidate location being location of the Type2 device; positioning the testing Type1 device at at least one candidate orientation in the testing venue, one of the candidate orientation being orientation of the Type1 device; and positioning the testing Type2 device at at least one candidate orientation in the testing venue, one of the candidate orientation being orientation of the Type2 device.

Clause 5. The method of configuring the wireless monitoring system of clause 3, further comprising: wherein the testing object comprises at least one of: the object, the object performing the motion, the object performing at least one target motion to be monitored in the monitoring task, a testing object similar to the object, a testing object with similar wireless footprint as the object, a testing object with similar wireless signature as the object, a testing object with similar wireless signature as the object with respect to the CI, a testing object with similar CI as the object, a testing object with similar physical appearance as the object, a testing object with similar physical structure as the object, a testing object with moveable parts similar to the object, a testing object capable of performing motions similar to the object, a testing object performing the motion, and a testing object performing at least one target motion to be monitored in the monitoring task; wherein the testing motion comprises at least one of: the motion of the object, a testing motion similar to the motion of the object, a part of the motion of the object, a partial testing motion similar to the part of the motion of the object, the motion of part of the object, a partial testing motion similar to the motion of the part of the object, the motion of moveable parts of the object, a testing motion of at least one moveable parts similar to the motion of corresponding moveable parts of the object, a part of the motion of moveable parts of the object, a partial testing motion similar to the part of the motion of corresponding moveable parts, the motion of moveable parts of part of the object, a testing motion of at least one moveable parts similar to the motion of corresponding moveable parts of the part of the object, and a target motion to be monitored in the monitoring task.

Clause 6. The method of configuring the wireless monitoring system of clause 3, further comprising: wherein the testing wireless signal comprises at least one candidate wireless signal, one of the candidate wireless signal being the wireless signal; wherein each candidate wireless signal is associated with at least one of: at least one transmitting antenna, at least one receiving antenna, a carrier frequency, a modulation, a signal constellation, a signal bandwidth, a frequency band, a frequency aggregation, a frequency hopping, a signaling, a signal format, a protocol, a standard, a series of sounding signals, a choice of sounding signals, a sounding frequency, a sounding rate, a sounding period, a sounding timing, a sounding timing regularity, a management frame, a control frame, a data frame, a management package, a control packet, a data packet, a frame control field, a field of a frame, a frame header, and a frame body.

Clause 7. The method of configuring the wireless monitoring system of clause 3, further comprising: choosing the system state to be the chosen admissible system states automatically based on an optimization criterion associated with the testing procedure and the monitoring of the testing object based on the set of testing CI.

Clause 8. The method of configuring the wireless monitoring system of clause 1: wherein the wireless signal comprises a series of sounding signals based on a protocol, wherein each admissible system state and its associated setting, are associated with at least one of: a timing, a lapse, a rate, a sounding rate, a sounding rhythm, a signal strength, a signal modulation, a carrier frequency, a frequency band, a frequency bandwidth, a frequency hopping, a transmit antenna, a receive antenna, a choice of the sounding signal, a choice of the CI, a monitoring functionality, a functionality level, and a functionality parameter, of at least one of: the Type1 device, the Type2 device, the coordination of the Type1 device and the Type2 device, the series of sounding signals, the set of CI and the monitoring of the object.

Clause 9. The method of configuring the wireless monitoring system of clause 1, further comprising: applying the setting by configuring at least one of: the Type1 device, the Type2 device, the other devices, an integrated circuit (IC) of the Type1 device, an IC of the Type2 device, an IC of one of the other devices, the coordination between any of: the Type1 device, the Type2 device and the other devices, the wireless signal, the signaling in the wireless signal, the sounding signals in the wireless signal, the timing or sounding frequency of the sounding signals, the transmission, at least one of: the reception, the generation or the processing, of the wireless signal, the set of CI, the obtaining of the set of CI, and the monitoring of the object, based on the system state.

Clause 10. The method of configuring the wireless monitoring system of clause 9, further comprising: configuring the Type1 device indirectly by configuring the Type2 device.

Clause 11. The method of configuring the wireless monitoring system of clause 10: wherein the wireless signal comprises the series of sounding signals in response to a series of triggering wireless signals from the Type2 device based on a protocol, each sounding signal being a triggered response to a triggering signal from the Type2 device based on the protocol, configuring at least one of: the triggered response, the series of sounding signals, and the transmission of the series of sounding signals, from the Type1 device indirectly by configuring the series of triggering signals transmitted by the Type2 device.

Clause 12. The method of configuring the wireless monitoring system of clause 11: configuring at least one of: a timing, a lapse, a rate, a sounding rate, a sounding rhythm, a signal strength, a signal modulation, a carrier frequency, a frequency band, a frequency bandwidth, a frequency hopping, an antenna, and a choice of the sounding signal, of the series of sounding signals of the Type1 device indirectly by configuring at least one of: a timing, a sounding rate, a sounding rhythm, a signal strength, a signal modulation, a carrier frequency, a frequency band, a frequency bandwidth, a frequency hopping, an antenna, and a choice of the sounding signal, of the series of triggering signals transmitted by the Type2 device.

Clause 13. The method of configuring the wireless monitoring system of clause 9: configuring the Type2 device indirectly by configuring the Type1 device.

Clause 14. The method of configuring the wireless monitoring system of clause 13: wherein the wireless signal comprises a series of sounding signals, configuring at least one of: the Type2 device, an extraction of the set of CI from the received wireless signal, and the set of CI, indirectly by configuring at least one of: a timing, a sounding rate, a sounding rhythm, a signal strength, a signal modulation, a carrier frequency, a frequency band, a frequency bandwidth, a frequency hopping, an antenna, and a choice of the sounding signal, of the Type1 device.

Clause 15. The method of configuring the wireless monitoring system of clause 1, further comprising at least one of: changing the system state to be another one of the admissible system states, or updating a setting associated with a particular admissible system state based on a change in at least one of: the Type1 device, the Type2 device, the wireless signal, the signaling, the sounding signals, the timing, the sounding frequency, the frame type, the field, the generation, the transmission, the reception, the processing, the coordination, the set of CI, the obtaining, the customization, the computation, the wireless multipath channel, and the venue.

Clause 16. The method of configuring the wireless monitoring system of clause 15, further comprising: changing the system state based on at least one of: a finite state machine (FSM), a trigger of state transition of the FSM, a criterion, an event, a condition, a schedule, a request, a requirement, an optimization, a goal, an operation, a discovery, a sensor reading, a status change, a trigger from another device, a time-out, a timing, a monitoring functionality, a functionality requirement, a computation requirement, a memory requirement, a sounding requirement, a functionality setting, a sensitivity setting, a resolution setting, a detection, a recognition, a monitoring, a monitored condition, a monitoring state, a monitored situation, a monitored quantity, a shared resource, a shared resource constraint, a resource management, a network congestion of the wireless multipath channel, an interference of the wireless multipath channel, another sensor, another sensor in the Type1 device, another sensor in the Type2 device, a power management, a heat management, a computation management, a memory management, a power on, a power off, a power efficiency consideration, a heat consideration, a network consideration, a traffic consideration of the wireless multipath channel, a usage consideration, a user consideration, a power saving, a heat reduction, a traffic congestion, a traffic optimization, a new condition of the monitoring task, a new stage of the monitoring task, a change of the monitoring task, a change of the object, an appearance of the object, a disappearance of the object, a change of the motion of the object, a change of the venue, a change of the wireless multipath channel, a change of the Type1 device, a change of the Type2 device, a situation of the venue, a situation of the wireless multipath channel, a situation of the Type1 device, a situation of the Type2 device, a new motion of the object to be monitored, a new monitoring task, or a new object to be monitored.

Clause 17. The method of configuring the wireless monitoring system of clause 15, further comprising: wherein the wireless signal comprises a series of sounding signals based on a protocol, wherein a sounding rate is associated with the series of sounding signals, changing the system state to a first state associated with a normal sounding rate associated with the monitoring task; changing the system state to a second state associated with a sounding rate higher than the normal rate when the monitoring task becomes demanding, changing the system state to a third state associated with a sounding rate lower than the normal rate to save power.

Clause 18. The method of configuring the wireless monitoring system of clause 15, further comprising: performing a first set of at least one monitoring task, wherein performing any monitoring task comprises monitoring a respective object and a corresponding motion of the respective object based on the set of CI; choosing the system state to be a first state based on the first set of monitoring task; performing a second set of at least one monitoring task instead of the first set of monitoring task; and changing the system state from the first state to a second state based on the second set of monitoring task.

Clause 19. The method of configuring the wireless monitoring system of clause 18, further comprising: wherein there are more than one monitoring tasks, comprising a default task and at least one on-demand task; choosing the system state to a first state associated with a first setting associated with the default monitoring task; changing the system state to a second state associated with a second setting associated with an on-demand task; changing the system state back to the first state after the on-demand task.

Clause 20. A method of configuring a wireless monitoring system, comprising: transmitting a wireless signal from a Type1 heterogeneous wireless device through a wireless multipath channel of a venue; receiving the wireless signal by a Type2 heterogeneous wireless device through the wireless multipath channel, wherein the received wireless signal differs from the transmitted wireless signal due to the wireless multipath channel of the venue and a modulation of the wireless signal by an object undergoing a motion in the venue; obtaining a set of channel information (CI) of the wireless multipath channel based on the received wireless signal using a processor, a memory and a set of instructions; performing a monitoring task by monitoring the object and the motion of the object based on the set of CI; determining a number of admissible system states of the wireless monitoring system, each admissible system state associated with a respective setting; and choosing a system state to be one of the admissible system states automatically based on the monitoring task; configuring the wireless monitoring system by applying the setting associated with the chosen admissible system state to at least one of: the Type1 device, the Type2 device, another Type1 device, another Type2 device, a server, a user device, an integrated circuit (IC) of a device, a coordination between at least two devices, the wireless signal, a signaling in the wireless signal, a series of sounding signals in the wireless signal, the timing or sounding frequency of the sounding signals, the transmission, at least one of: reception, generation or processing, of the wireless signal, the set of CI, the obtaining of the set of CI, and the monitoring of the object, based on the system state.

Clause 21. The method of configuring the wireless monitoring system of clause 20, comprising: choosing the system state to be the chosen admissible system state automatically based on at least one of: at least one of: a negotiation, a handshake, or a coordination, between at least two of: the Type1 device, the Type2 device, a server, another Type1 device or another Type2 device, at least one of: a constraint, a requirement and a condition of the monitoring task, at least one of: a command, a request, a coordination, and a planning of a server, a testing procedure, or an optimization criterion.

Clause 22. The method of configuring the wireless monitoring system of clause 20, comprising: performing a testing procedure associated with the monitoring task; transmitting a testing wireless signal from a testing Type1 heterogeneous wireless device through a testing wireless multipath channel of a testing venue; receiving the testing wireless signal by a testing Type2 heterogeneous wireless device through the testing wireless multipath channel, wherein the received testing wireless signal differs from the transmitted testing wireless signal due to the testing wireless multipath channel of the testing venue and a modulation of the testing wireless signal by a testing object undergoing a testing motion in the testing venue; obtaining a set of testing channel information (CI) of the testing wireless multipath channel based on the received testing wireless signal using a testing processor, a testing memory and a set of testing instructions; performing the testing procedure by monitoring the testing object and the testing motion of the testing object based on the set of testing CI; and choosing the system state to be the chosen admissible system states automatically based on the testing procedure and an associated optimization criterion.

Clause 23. The method of configuring the wireless monitoring system of clause 20, further comprising at least one of: wherein the wireless signal comprises a series of sounding signals based on a protocol, wherein a sounding rate is associated with the series of sounding signals, changing the system state to a first state associated with a normal sounding rate associated with the monitoring task; changing the system state to a second state associated with a sounding rate higher than the normal rate when the monitoring task becomes demanding; or changing the system state to a third state associated with a sounding rate lower than the normal rate to save power.

Clause 24. The method of configuring the wireless monitoring system of clause 20, further comprising: performing a first set of at least one monitoring task, wherein performing any monitoring task comprises monitoring a respective object and a corresponding motion of the respective object based on the set of CI; choosing the system state to be a first state based on the first set of monitoring task; performing a second set of at least one monitoring task instead of the first set of monitoring task; and changing the system state from the first state to a second state based on the second set of monitoring task.

Clause 25. A wireless monitoring system, comprising: a Type1 heterogeneous wireless device which is configured to transmit a wireless signal through a wireless multipath channel of a venue; a Type2 heterogeneous wireless device which is configured using a processor, a memory and a set of instructions to: receive the wireless signal through the wireless multipath channel, wherein the received wireless signal differs from the transmitted wireless signal due to the wireless multipath channel of the venue and a modulation of the wireless signal by an object undergoing a motion in the venue, obtain a set of channel information (CI) of the wireless multipath channel based on the received wireless signal, perform a monitoring task by monitoring the object and the motion of the object based on the set of CI, wherein a number of admissible system states of the wireless monitoring system is being determined, each admissible system state associated with a respective setting of at least one of: the wireless signal, a signaling in the wireless signal, a series of sounding signals in the wireless signal, a timing of the sounding signals in the wireless signal, a sounding frequency of the sounding signals, a frame type of the wireless signal, a field of the frame type of the wireless signal, a generation of the wireless signal by the Type1 device, a transmission of the wireless signal by the Type1 device, a reception of the wireless signal by the Type2 device, a processing of the wireless signal by the Type2 device, a coordination of the Type1 device and the Type2 device regarding the transmission of the wireless signal, a coordination with other devices regarding the transmission of the wireless signal, the set of CI, the obtaining of the set of CI of the wireless multipath channel based on the received wireless signal, the monitoring task of the object, a customization of the monitoring task, a computation for the monitoring task, a computation for monitoring the object based on the CI, wherein a system state is chosen to be one of the admissible system states based on the monitoring task, wherein the wireless monitoring system is configured by applying a setting associated with the chosen admissible system state to at least one of: the Type1 device, the Type2 device, another Type1 device, another Type2 device, a server, a user device, an integrated circuit (IC) of a device, a coordination between at least two devices, the wireless signal, a signaling in the wireless signal, a series of sounding signals in the wireless signal, the timing or sounding frequency of the sounding signals, the transmission, at least one of: reception, generation or processing, of the wireless signal, the set of CI, the obtaining of the set of CI, and the monitoring of the object, based on the system state.

Clause 26. The wireless monitoring system of clause 25, wherein: the system state is chosen to be the chosen admissible system state based on at least one of: at least one of: a negotiation, a handshake, or a coordination, between at least two of: the Type1 device, the Type2 device, a server, another Type1 device or another Type2 device, at least one of: a constraint, a requirement and a condition of the monitoring task, at least one of: a command, a request, a coordination, and a planning of a server, a testing procedure, or an optimization criterion.

Clause 27. The wireless monitoring system of clause 25, wherein: a testing procedure is performed associated with the monitoring task; a testing wireless signal is transmitted from a testing Type1 heterogeneous wireless device through a testing wireless multipath channel of a testing venue; the testing wireless signal is received by a testing Type2 heterogeneous wireless device through the testing wireless multipath channel, wherein the received testing wireless signal differs from the transmitted testing wireless signal due to the testing wireless multipath channel of the testing venue and a modulation of the testing wireless signal by a testing object undergoing a testing motion in the testing venue; a set of testing channel information (CI) of the testing wireless multipath channel is obtained based on the received testing wireless signal using a testing processor, a testing memory and a set of testing instructions; the testing procedure is performed by monitoring the testing object and the testing motion of the testing object based on the set of testing CI; and the system state is chosen to be the chosen admissible system states based on the testing procedure and an associated optimization criterion.

Clause 28. The wireless monitoring system of clause 25, wherein: the system state is changed to another one of the admission system states by applying a setting based on at least one of: a finite state machine (FSM), a trigger of state transition of the FSM, a criterion, an event, a condition, a schedule, a request, a requirement, an optimization, a goal, an operation, a discovery, a sensor reading, a status change, a trigger from another device, a time-out, a timing, a monitoring functionality, a functionality requirement, a computation requirement, a memory requirement, a sounding requirement, a functionality setting, a sensitivity setting, a resolution setting, a detection, a recognition, a monitoring, a monitored condition, a monitoring state, a monitored situation, a monitored quantity, a shared resource, a shared resource constraint, a resource management, a network congestion of the wireless multipath channel, an interference of the wireless multipath channel, another sensor, another sensor in the Type1 device, another sensor in the Type2 device, a power management, a heat management, a computation management, a memory management, a power on, a power off, a power efficiency consideration, a heat consideration, a network consideration, a traffic consideration of the wireless multipath channel, a usage consideration, a user consideration, a power saving, a heat reduction, a traffic congestion, a traffic optimization, a new condition of the monitoring task, a new stage of the monitoring task, a change of the monitoring task, a change of the object, an appearance of the object, a disappearance of the object, a change of the motion of the object, a change of the venue, a change of the wireless multipath channel, a change of the Type1 device, a change of the Type2 device, a situation of the venue, a situation of the wireless multipath channel, a situation of the Type1 device, a situation of the Type2 device, a new motion of the object to be monitored, a new monitoring task, or a new object to be monitored.

Clause 29. The wireless monitoring system of clause 25, wherein: a setting associated with a particular admissible system state is updated based on a change in at least one of: the Type1 device, the Type2 device, the another Type1 device, the another Type2 device, the server, the user device, the IC, the coordination between the at least two devices, the wireless signal, the signaling, the sounding signals, the timing, the sounding frequency, the frame type, the field, at least one of: the generation, the transmission, the reception, or the processing of the wireless signal, the set of CI, the obtaining, the customization, the computation, the wireless multipath channel, and the venue.

Clause 30. A Type2 heterogeneous wireless device of a wireless monitoring system, comprising: a wireless receiver; a processor communicatively coupled with the wireless receiver; a memory communicatively coupled with the processor; a set of instructions stored in the memory which, when executed by the processor, causes the Type2 heterogeneous wireless device to: receive a wireless signal through a wireless multipath channel of a venue, wherein the wireless signal is transmitted by a Type1 heterogeneous wireless device through the wireless multipath channel, wherein the received wireless signal differs from the transmitted wireless signal due to the wireless multipath channel of the venue and a modulation of the wireless signal by an object undergoing a motion in the venue, obtain a set of channel information (CI) of the wireless multipath channel based on the received wireless signal, perform a monitoring task by monitoring the object and the motion of the object based on the set of CI, wherein a number of admissible system states of the wireless monitoring system are determined, each admissible system state associated with a respective setting of at least one of: the wireless signal, a signaling in the wireless signal, a series of sounding signals in the wireless signal, a timing of the sounding signals in the wireless signal, a sounding frequency of the sounding signals, a frame type of the wireless signal, a field of the frame type of the wireless signal, a generation of the wireless signal by the Type1 device, a transmission of the wireless signal by the Type1 device, a reception of the wireless signal by the Type2 device, a processing of the wireless signal by the Type2 device, a coordination of the Type1 device and the Type2 device regarding the transmission of the wireless signal, a coordination with other devices regarding the transmission of the wireless signal, the set of CI, the obtaining of the set of CI of the wireless multipath channel based on the received wireless signal, the monitoring task of the object, a customization of the monitoring task, a computation for the monitoring task, a computation for monitoring the object based on the CI; wherein a system state is chosen to be one of the admissible system states based on the monitoring task; wherein the wireless monitoring system is configured by applying a setting associated with the chosen admissible system state to at least one of: the Type1 device, the Type2 device, another Type1 device, another Type2 device, a server, a user device, an integrated circuit (IC) of a device, a coordination between at least two devices, the wireless signal, a signaling in the wireless signal, a series of sounding signals in the wireless signal, the timing or sounding frequency of the sounding signals, the transmission, at least one of: reception, generation or processing, of the wireless signal, the set of CI, the obtaining of the set of CI, and the monitoring of the object, based on the system state.

Clause 31. A method of configuring the wireless monitoring system, comprising: transmitting a wireless signal from a Type1 heterogeneous wireless device through a wireless multipath channel of a venue; receiving the wireless signal by a Type2 heterogeneous wireless device through the wireless multipath channel, wherein the received wireless signal differs from the transmitted wireless signal due to the wireless multipath channel of the venue and a modulation of the wireless signal by an object in the venue; obtaining a set of channel information (CI) of the wireless multipath channel based on the received wireless signal using a processor, a memory communicatively coupled with the processor and a set of instructions stored in the memory; monitoring the object based on the set of CI; estimating the monitoring of the object in a reproducible manner by monitoring a mechanical replacement object in place of the object using the same system in the same way.

Clause 32. The method of configuring the wireless monitoring system of clause 1, comprising: replacing the object with the mechanical replacement object by removing the object and positioning the mechanical replacement object at the same location in the same way in the venue; transmitting a second wireless signal from the Type1 heterogeneous wireless device through the wireless multipath channel of the venue; receiving the second wireless signal by the Type2 heterogeneous wireless device through the wireless multipath channel, wherein the received second wireless signal differs from the transmitted second wireless signal due to the wireless multipath channel of the venue and a modulation of the second wireless signal by the replacement object in the venue; obtaining a second set of channel information (CI) of the wireless multipath channel based on the received second wireless signal using the processor, the memory communicatively coupled with the processor and the set of instructions stored in the memory; monitoring the mechanical replacement object based on the second set of CI.

Clause 33. The method of configuring the wireless monitoring system of clause 1 or clause 11: wherein the mechanical replacement object comprises at least one of: a mechanical structure to support a mechanical covering, a mechanical structure with a similar shape as the object, a mechanical structure with a similar surface as the object, a mechanical structure with a similar surface texture as the object, a mechanical structure with a similar reflective surface as the object, a mechanical structure with a similar skeleton as the object, a mechanical structure with a similar structure as the object, a mechanical structure with a similar cavity as the object, a mechanical covering with a similar wireless property as a covering of the object, a mechanical covering at a structure with a similar wireless property as a corresponding structure of the object, a mechanical covering at a surface with a similar wireless property as a corresponding surface of the object, a mechanical covering at a skeleton with a similar wireless property as a corresponding skeleton of the object, a mechanical covering at a cavity with a similar wireless property as a corresponding cavity of the object, a mechanical covering at a surface of the mechanical replacement object to amplify wireless reflection, a movable mechanism capable of make a similar motion as the object, a mechanical covering with a similar wireless property as the object in their respective motion, a material with similar wireless property as human flesh, and another wireless characteristics.

Clause 34. The method of configuring the wireless monitoring system of clause 1: wherein the object is a living object (e.g. human, pet); wherein the mechanical replacement object comprises at least one of: a specific anthropomorphic mannequin (SAM), a mechanical doll with movable chest to mimic breathing, a mannequin with a covering with similar monitoring characteristics of the object in the wireless multipath channel, a mannequin with a covering with similar monitoring characteristics of the object in the wireless multipath channel with respect to the set of CI, a mannequin with a covering to mimic wireless property of the object in the wireless multipath channel, a mannequin with a covering to mimic radio reflection of the object, a mannequin with a covering to mimic radio refraction of the object, a mannequin with a covering to mimic radio absorption of the object, a mannequin with a covering to mimic radio transmission through the object, a mannequin with a covering to mimic radio propagation through the object, a mannequin with moveable chest to mimic breathing, a mannequin with moveable joints, a mannequin with moveable limbs, a mannequin with moveable head, a mannequin with moveable mouth, a mannequin with moveable hands, a mannequin with moveable fingers, a mannequin with moveable legs, a mannequin with moveable feet, a mannequin with moveable bones, a mannequin with moveable muscles, a mannequin with liquid content, a robot that can mimic at least one of: human motion, human gait, human gesture, animal motion, animal gait, animal gesture, and another mechanical imitation of the object.

Clause 35. The method of configuring the wireless monitoring system of clause 1: wherein the mechanical replacement object comprises at least one of: a mechanical adult male, a mechanical adult female, a mechanical older adult, a mechanical adult with strong build, a mechanical adult with medium build, a mechanical adult with small build, a mechanical boy, a mechanical girl, a mechanical baby, a mechanical limb, a mechanical hand, a mechanical arm, a mechanical leg, a mechanical foot, a mechanical torso, a mechanical head, a mechanical upper body, a mechanical lower body, a mechanical joint, a mechanical body, a mechanical animal, a mechanical pet, a mechanical cat, a mechanical dog, a mechanical vehicle, a mechanical vehicle replica, and another mechanical replica.

Clause 36. The method of configuring the wireless monitoring system of clause 1, comprising: computing a transformation of the monitoring of the mechanical replacement object to estimate the monitoring of the object.

Clause 37. The method of configuring the wireless monitoring system of clause 1, comprising: wherein the transformation is associated with at least one of: a model, a material of the mechanical replacement object, a property of the mechanical replacement object.

Clause 38. The method of configuring the wireless monitoring system of clause 1, comprising: wherein the received wireless signal differs from the transmitted wireless signal further due to a modulation of the wireless signal by a motion of an object in the venue; monitoring the motion of the object based on the set of CI; estimating the monitoring of the motion of the object in a reproducible manner by monitoring a similar motion of the mechanical replacement object in place of the motion of the object using the same system.

Clause 39. The method of configuring the wireless monitoring system of clause 1, comprising: computing a transformation of the monitoring of the motion of mechanical replacement object to the monitoring of the motion of the object.

Clause 40. The method of configuring the wireless monitoring system of clause 1, comprising: wherein the transformation is associated with at least one of: a model, a model of the venue, a model of the object, a model of the mechanical replacement object, a model of motion of the object, a model of motion of the mechanical replacement object, a material of the mechanical replacement object, a property of the mechanical replacement object, a robotic characteristics of the mechanical replacement object, and a characteristics of a mechanical movement of the mechanical replacement object.

Clause 41. A method of configuring the wireless monitoring system, comprising: transmitting a wireless signal from a Type1 heterogeneous wireless device through a wireless multipath channel of a venue; receiving the wireless signal by a Type2 heterogeneous wireless device through the wireless multipath channel, wherein the received wireless signal differs from the transmitted wireless signal due to the wireless multipath channel of the venue and a modulation of the wireless signal by a replacement object in the venue, wherein the replacement object is a mechanical replacement of an object in the venue; obtaining a set of channel information (CI) of the wireless multipath channel based on the received wireless signal using a processor, a memory communicatively coupled with the processor and a set of instructions stored in the memory; estimating a monitoring of the object by the wireless monitoring system by monitoring the replacement object in the venue in a reproducible manner based on the set of CI.

Clause 42. The method of configuring the wireless monitoring system of clause 7, comprising: wherein the received wireless signal differs from the transmitted wireless signal further due to a modulation of the wireless signal by a motion of the object in the venue; estimating a monitoring of a motion of the object by the wireless monitoring system by monitoring a similar motion of the replacement object in the venue in a reproducible manner based on the set of CI; estimating a monitoring of a motion of the object in a reproducible manner by monitoring the same motion of the mechanical replacement object in place of the motion of the object using the same system.

Clause 43. The method of configuring the wireless monitoring system of clause 4, further comprising: wherein the testing Type1 device comprises at least one of: the Type1 device, another Type1 device, the Type2 device, another Type2 device and another wireless device; wherein the testing Type2 device comprises at least one of: the Type1 device, another Type1 device, the Type2 device, another Type2 device and another wireless device; positioning the testing Type1 device at at least one candidate location in the testing venue, one of the candidate location being location of the Type1 device; positioning the testing Type2 device at at least one candidate location in the testing venue, one of the candidate location being location of the Type2 device; positioning the testing Type1 device at at least one candidate orientation in the testing venue, one of the candidate orientation being orientation of the Type1 device; positioning the testing Type2 device at at least one candidate orientation in the testing venue, one of the candidate orientation being orientation of the Type2 device; wherein the testing object comprises at least one of: the object, a testing object similar to the object, a testing object with similar wireless footprint as the object, a testing object with similar wireless signature as the object, a testing object with similar wireless signature as the object with respect to the CI, a testing object with similar CI as the object, a testing object with moveable joints similar to the object, a testing object capable of performing motions of the object, a human, a human-like mannequin, a mannequin with similar wireless footprint as the human, a mannequin with similar wireless signature as the human, a mannequin with similar wireless signature as the human with respect to the CI, a mannequin with similar CI as the human, a mannequin with moveable joints similar to the human, a mannequin capable of performing motions of the human, a part of the human, a human-like mannequin, a mannequin mimicking the human, a mannequin mimicking the part of the human, a mannequin with similar wireless footprint as the human, a mannequin with similar wireless signature as the human, a mannequin with similar wireless signature as the human with respect to the CI, a mannequin with similar CI as the human, a mannequin with moveable joints similar to the human, a mannequin capable of performing motions of the human, moving the test object such that at least one of: a testing object with similar motion behavior as the object, a testing object undergoing a similar motion as the object; wherein the testing venue comprises at least one of: the venue, the venue in a testing condition, the venue in at least one candidate operating condition, the venue in at least one candidate manifestation, the venue in at least one candidate expression, the venue without the object, the venue with the object in at least one candidate expression, the venue with the testing object similar to the object wherein the testing wireless signal comprises at least one candidate wireless signal, one of the candidate wireless signal being the wireless signal; wherein the testing wireless multipath channel comprises at least one of: the wireless multipath channel or other admissible wireless channel; wherein the testing venue comprises the venue or another.

Clause P1. A method/system/software/device of a wireless monitoring system, comprising: transmitting a wireless signal from a Type 1 heterogeneous wireless device through a wireless multipath channel of a venue; receiving the wireless signal by a Type 2 heterogeneous wireless device through the wireless multipath channel, wherein the received wireless signal differs from the transmitted wireless signal due to the wireless multipath channel of the venue and a modulation of the wireless signal by an object in the venue; obtaining a set of channel information (CI) of the wireless multipath channel based on the received wireless signal using a processor, a memory communicatively coupled with the processor and a set of instructions stored in the memory; monitoring the object based on the set of CI; determining a number of admissible system states each associated with a respective system setting of at least one of: the wireless signal, the transmission of the wireless signal by the Type 1 device, the reception of the wireless signal by the Type 2 device, a coordination of the Type 1 device and the Type 2 device regarding the transmission of the wireless signal, the set of CI, the obtaining of the set of CI of the wireless multipath channel, and the monitoring of the object; and setting a system state of the wireless monitoring system to be one of the admissible system states by applying the system setting associated with the admissible system state to the wireless monitoring system.

Clause P2. The method/system/software/device of the wireless monitoring system of Clause P1, further comprising: applying the system setting by configuring at least one of: the Type 1 device, the Type 2 device, the coordination of the Type 1 device and the Type 2 device, the wireless signal, the transmission and reception of the wireless signal, the set of CI, the obtaining of the set of CI, and the monitoring of the object, based on the system setting.

Clause P3. The method/system/software/device of the wireless monitoring system of Clause P1: configuring the Type 1 device indirectly by configuring the Type 2 device.

Clause P4. The method/system/software/device of the wireless monitoring system of Clause P3: wherein the wireless signal comprises a series of sounding signals in responses to a series of triggering wireless signals from the Type 2 device based on a protocol, each sounding signal being a triggered response to a triggering signal from the Type 2 device based on the protocol, configuring at least one of: the triggered response, the series of sounding signals, and the transmission of the series of sounding signals, from the Type 1 device indirectly by configuring the series of triggering signal transmitted by the Type 2 device.

Clause P5. The method/system/software/device of the wireless monitoring system of Clause P4: configuring at least one of: a timing, a lapse, a sounding rate, a sounding rhythm, a signal strength, a signal modulation, a carrier frequency, a frequency band, a frequency bandwidth, a frequency hopping, an antenna, and a choice of the sounding signal, of the series of sounding signals by the Type 1 device indirectly by configuring at least one of: a timing, a sounding rate, a sounding rhythm, a signal strength, a signal modulation, a carrier frequency, a frequency band, a frequency bandwidth, a frequency hopping, an antenna, and a choice of the sounding signal, of the series of triggering signal transmitted by the Type 2 device.

Clause P6. The method/system/software/device of the wireless monitoring system of Clause P1: configuring the Type 2 device indirectly by configuring the Type 1 device.

Clause P7. The method/system/software/device of the wireless monitoring system of Clause P1: wherein the wireless signal comprises a series of sounding signals, configuring at least one of: the Type 2 device, an extraction of the set of CI from the received wireless signal, and the set of CI, indirectly by configuring at least one of: a timing, a sounding rate, a sounding rhythm, a signal strength, a signal modulation, a carrier frequency, a frequency band, a frequency bandwidth, a frequency hopping, an antenna, and a choice of the sounding signal, of the Type 1 device.

Clause P8. The method/system/software/device of the wireless monitoring system of Clause P1: wherein the wireless signal comprises a series of sounding signals based on a protocol, wherein at least one of: an admissible system state, and a system setting, is associated with at least one of: a timing, a rate, a sounding rate, a sounding rhythm, a signal strength, a signal modulation, a carrier frequency, a frequency band, a frequency bandwidth, a frequency hopping, a transmit antenna, a receive antenna, a choice of the sounding signal, a choice of the CI, a monitoring functionality, a functionality level, a functionality parameter, of at least one of: the Type 1 device, the Type 2 device, the coordination of the Type 1 device and the Type 2 device, the series of sounding signals, the set of CI and the monitoring of the object.

Clause P9. The method/system/software/device of the wireless monitoring system of Clause P1: wherein the set of CI comprises at least one of: a channel state information (CSI), a channel impulse response (CIR), a channel frequency response (CFR), a received signal strength indicator (RSSI), an angle of arrival (AoA), a time of arrival (ToF) and another channel information.

Clause P10. The method/system/software/device of the wireless monitoring system of Clause P1: wherein a CI is associated with a transmitter antenna of the Type 1 device and a receive antenna of the Type 2 device.

Clause P11. The method/system/software/device of the wireless monitoring system of Clause P1, further comprising: changing the system state to be another admissible system state by applying the system setting associated with the another admissible system state to the wireless monitoring system.

Clause P12. The method/system/software/device of the wireless monitoring system of Clause P11, further comprising: changing the system state based on at least one of: a finite state machine (FSM), a trigger of state transition of the FSM, a criterion, an event, a condition, a schedule, a request, a requirement, an optimization, a goal, an operation, a discovery, a sensor reading, a status change, a trigger from another device, a time-out, a timing, a monitoring functionality, a functionality requirement, a computation requirement, a memory requirement, a sounding requirement, a functionality setting, a sensitivity setting, a resolution setting, a detection, a recognition, a monitoring, a monitored condition, a monitoring state, a monitored situation, a monitored quantity, a shared resource, a shared resource constraint, a resource management, a network congestion of the wireless multipath channel, an interference of the wireless multipath channel, another sensor, another sensor in the Type 1 device, another sensor in the Type 2 device, a power management, a heat management, a computation management, a memory management, a power on, a power off, a power efficiency consideration, a heat consideration, a network consideration, a traffic consideration of the wireless multipath channel, a usage consideration, a user consideration, a power saving, a heat reduction, a traffic congestion, a traffic optimization, and another trigger.

Clause P13. The method/system/software/device of the wireless monitoring system of Clause P1, further comprising: wherein the wireless signal comprises a series of sounding signals based on a protocol, changing at least one of: a timing, a lapse, a rate, a sounding rate, a sounding rhythm, a signal strength, a signal modulation, a carrier frequency, a frequency band, a frequency bandwidth, a frequency hopping, a transmit antenna, a receive antenna, a choice of the sounding signal, a choice of the CI, a monitoring functionality, a functionality level, a functionality parameter, of at least one of: the Type 1 device, the Type 2 device, the coordination of the Type 1 device and the Type 2 device, the series of sounding signals, the set of CI and the monitoring of the object, by changing at least one of: the system state and the system setting.

Clause P14. The method/system/software/device of the wireless monitoring system of Clause P1, further comprising: wherein the wireless signal comprises a series of sounding signals based on a protocol, wherein a sounding rate is associated with the series of sounding signals, changing the system state to a first state associated with a normal sounding rate associated with the monitoring of the object; changing the system state to a second state associated with a sounding rate higher than the normal rate when the monitoring of the object becomes demanding, changing the system state to a third state associated with a sounding rate lower than the normal rate to save power.

Clause P15. The method/system/software/device of the wireless monitoring system of Clause P1: wherein there is at least one monitoring task, comprising at least one of: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, breathing tracking, human breathing detection, human breathing recognition, human breathing estimation, breathing detection, breathing tracking, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, motion categorization, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, motion localization, room sensing, tracking, multiple object tracking, indoor tracking, indoor position, indoor navigation, energy management, power transfer, wireless power transfer, object counting, car tracking in parking garage, activating a device or a system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task.

Clause P16. The method/system/software/device of the wireless monitoring system of Clause P14, further comprising: wherein there are at least one monitoring task; changing the system state to a state associated with a system setting associated with one of the monitoring task.

Clause P17. The method/system/software/device of the wireless monitoring system of Clause P14, further comprising: wherein there are at least one monitoring task; changing the system state to a state associated with a system setting associated with at least one of the following monitoring task: motion detection, presence detection, home monitoring, public space monitoring, periodic motion monitoring, transient motion monitoring, breathing monitoring, heart beat monitoring, vital sign monitoring, counting, well-being monitoring, sleep monitoring, daily activity monitoring, apnea detection, medical condition detection, fall-down detection, speed measuring, a gait recognition task, a motion recognition task, a radio biometric task, security event detection, suspicious event detection, intruder detection, locationing, tracking, navigation, motion localization, distance estimation, angle estimation, material determination, object determination, child presence detection in vehicle, driver recognition, driver sleepiness detection, radio frequency imaging, posture recognition, keystroke recognition, handwriting recognition, and another task.

Clause P18. The method/system/software/device of the wireless monitoring system of Clause P1, further comprising: wherein there are more than one monitoring tasks, comprising a default task and at least one on-demand task; setting the system state to a first state associated with a first setting associated with the default monitoring task; changing the system state to a second state associated with a second setting associated with an on-demand task; changing the system state back to the first state after the on-demand task.

Clause P19. The method/system/software/device of the wireless monitoring system of Clause P1, further comprising: wherein there are more than one monitoring states associated with the monitoring of the object based on the set of CSI; setting the system state based on the monitoring state.

Clause P20. The method/system/software/device of the wireless monitoring system of Clause P16, further comprising: setting the system state based on a current monitoring state; changing the system state to a second state associated with a new monitoring state.

Clause P21. A method/system/software/device of a wireless monitoring system, comprising: transmitting a wireless signal from a Type 1 heterogeneous wireless device through a wireless multipath channel of a venue; receiving the wireless signal by a Type 2 heterogeneous wireless device through the wireless multipath channel, wherein the received wireless signal differs from the transmitted wireless signal due to the wireless multipath channel of the venue and a modulation of the wireless signal by an object in the venue; obtaining a set of channel information (CI) of the wireless multipath channel based on the received wireless signal using a processor, a memory communicatively coupled with the processor and a set of instructions stored in the memory; monitoring the object based on the set of CI; estimating the monitoring of the object in a reproducible manner by monitoring a mechanical replacement object in place of the object using the same system in the same way.

Clause P22. The method/system/software/device of a wireless monitoring system of Clause P1, comprising: replacing the object with the mechanical replacement object by removing the object and positioning the mechanical replacement object at the same location in the same way in the venue; transmitting a second wireless signal from the Type 1 heterogeneous wireless device through the wireless multipath channel of the venue; receiving the second wireless signal by the Type 2 heterogeneous wireless device through the wireless multipath channel, wherein the received second wireless signal differs from the transmitted second wireless signal due to the wireless multipath channel of the venue and a modulation of the second wireless signal by the replacement object in the venue; obtaining a second set of channel information (CI) of the wireless multipath channel based on the received second wireless signal using the processor, the memory communicatively coupled with the processor and the set of instructions stored in the memory; monitoring the mechanical replacement object based on the second set of CI.

Clause P23. The method/system/software/device of a wireless monitoring system of Clause P1 or Clause P11: wherein the mechanical replacement object comprises at least one of: a mechanical structure to support a mechanical covering, a mechanical structure with a similar shape as the object, a mechanical structure with a similar surface as the object, a mechanical structure with a similar surface texture as the object, a mechanical structure with a similar reflective surface as the object, a mechanical structure with a similar skeleton as the object, a mechanical structure with a similar structure as the object, a mechanical structure with a similar cavity as the object, a mechanical covering with a similar wireless property as a covering of the object, a mechanical covering at a structure with a similar wireless property as a corresponding structure of the object, a mechanical covering at a surface with a similar wireless property as a corresponding surface of the object, a mechanical covering at a skeleton with a similar wireless property as a corresponding skeleton of the object, a mechanical covering at a cavity with a similar wireless property as a corresponding cavity of the object, a mechanical covering at a surface of the mechanical replacement object to amplify wireless reflection, a movable mechanism capable of make a similar motion as the object, a mechanical covering with a similar wireless property as the object in their respective motion, a material with similar wireless property as human flesh, and another wireless characteristics.

Clause P24. The method/system/software/device of a wireless monitoring system of Clause P1: wherein the object is a living object (e.g. human, pet); wherein the mechanical replacement object comprises at least one of: a specific anthropomorphic mannequin (SAM), a mechanical doll with movable chest to mimic breathing, a mannequin with a covering with similar monitoring characteristics of the object in the wireless multipath channel, a mannequin with a covering with similar monitoring characteristics of the object in the wireless multipath channel with respect to the set of CI, a mannequin with a covering to mimic wireless property of the object in the wireless multipath channel, a mannequin with a covering to mimic radio reflection of the object, a mannequin with a covering to mimic radio refraction of the object, a mannequin with a covering to mimic radio absorption of the object, a mannequin with a covering to mimic radio transmission through the object, a mannequin with a covering to mimic radio propagation through the object, a mannequin with moveable chest to mimic breathing, a mannequin with moveable joints, a mannequin with moveable limbs, a mannequin with moveable head, a mannequin with moveable mouth, a mannequin with moveable hands, a mannequin with moveable fingers, a mannequin with moveable legs, a mannequin with moveable feet, a mannequin with moveable bones, a mannequin with moveable muscles, a mannequin with liquid content, a robot that can mimic at least one of: human motion, human gait, human gesture, animal motion, animal gait, animal gesture, and another mechanical imitation of the object.

Clause P25. The method/system/software/device of a wireless monitoring system of Clause P1: wherein the mechanical replacement object comprises at least one of: a mechanical adult male, a mechanical adult female, a mechanical older adult, a mechanical adult with strong build, a mechanical adult with medium build, a mechanical adult with small build, a mechanical boy, a mechanical girl, a mechanical baby, a mechanical limb, a mechanical hand, a mechanical arm, a mechanical leg, a mechanical foot, a mechanical torso, a mechanical head, a mechanical upper body, a mechanical lower body, a mechanical joint, a mechanical body, a mechanical animal, a mechanical pet, a mechanical cat, a mechanical dog, a mechanical vehicle, a mechanical vehicle replica, and another mechanical replica.

Clause P26. The method/system/software/device of a wireless monitoring system of Clause P1, comprising: computing a transformation of the monitoring of the mechanical replacement object to estimate the monitoring of the object.

Clause P27. The method/system/software/device of a wireless monitoring system of Clause P1, comprising: wherein the transformation is associated with at least one of: a model, a material of the mechanical replacement object, a property of the mechanical replacement object.

Clause P28. The method/system/software/device of a wireless monitoring system of Clause P1, comprising: wherein the received wireless signal differs from the transmitted wireless signal further due to a modulation of the wireless signal by a motion of an object in the venue; monitoring the motion of the object based on the set of CI; estimating the monitoring of the motion of the object in a reproducible manner by monitoring a similar motion of the mechanical replacement object in place of the motion of the object using the same system.

Clause P29. The method/system/software/device of a wireless monitoring system of Clause P1, comprising: computing a transformation of the monitoring of the motion of mechanical replacement object to the monitoring of the motion of the object.

Clause P30. The method/system/software/device of a wireless monitoring system of Clause P1, comprising: wherein the transformation is associated with at least one of: a model, a model of the venue, a model of the object, a model of the mechanical replacement object, a model of motion of the object, a model of motion of the mechanical replacement object, a material of the mechanical replacement object, a property of the mechanical replacement object, a robotic characteristics of the mechanical replacement object, and a characteristics of a mechanical movement of the mechanical replacement object.

Clause P31. A method/system/software/device of a wireless monitoring system, comprising: transmitting a wireless signal from a Type 1 heterogeneous wireless device through a wireless multipath channel of a venue; receiving the wireless signal by a Type 2 heterogeneous wireless device through the wireless multipath channel, wherein the received wireless signal differs from the transmitted wireless signal due to the wireless multipath channel of the venue and a modulation of the wireless signal by a replacement object in the venue, wherein the replacement object is a mechanical replacement of an object in the venue; obtaining a set of channel information (CI) of the wireless multipath channel based on the received wireless signal using a processor, a memory communicatively coupled with the processor and a set of instructions stored in the memory; estimating a monitoring of the object by the wireless monitoring system by monitoring the replacement object in the venue in a reproducible manner based on the set of CI.

Clause P32. The method/system/software/device of a wireless monitoring system of Clause P7, comprising: wherein the received wireless signal differs from the transmitted wireless signal further due to a modulation of the wireless signal by a motion of the object in the venue; estimating a monitoring of a motion of the object by the wireless monitoring system by monitoring a similar motion of the replacement object in the venue in a reproducible manner based on the set of CI; estimating a monitoring of a motion of the object in a reproducible manner by monitoring the same motion of the mechanical replacement object in place of the motion of the object using the same system.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A method to perform a task comprising sub-tasks, implemented by a wireless monitoring system having a processor, a memory communicatively coupled with the processor, and a set of instructions stored in the memory to be executed by the processor, comprising:
    determining, by the processor, a collection of sub-tasks comprising: motion detection, presence detection, proximity detection, object recognition, transient motion monitoring, breathing monitoring, heart beat monitoring, well-being monitoring, counting, fall-down detection, speed measuring, gait recognition, motion recognition, radio biometric based recognition, security event detection, locationing, tracking, navigation, motion localization, distance estimation, angle estimation, material determination, object determination, daily activity monitoring, sleep monitoring, driver sleepiness detection, radio frequency imaging, gesture recognition, keystroke recognition, and handwriting recognition;
    determining, by the processor, a plurality of selectable system states of the wireless monitoring system, wherein
        each selectable system state comprises a corresponding set of sub-tasks selected from the collection of sub-tasks to be performed by the wireless monitoring system and a corresponding set of settings of the wireless monitoring system for performing the corresponding set of sub-tasks of the task,
        a first selectable system state, which is a default state to monitor daily activities of a user, comprises a particular collection of sub-tasks, comprising motion detection and breathing, of the task and a first set of settings, comprising a first sounding frequency, of the wireless monitoring system,
        a second selectable system state, which is a low-activity state to monitor the user when sleeping is detected, comprises the particular collection of sub-tasks and a second set of settings, comprising a second sounding frequency lower than the first sounding frequency, of the wireless monitoring system,
        a third selectable system state, which is an alarmed state to monitor the user during an alarmed situation, comprises the particular collection of sub-tasks, a sub-task of fall-down detection not in the particular collection, and a third set of settings, comprising a third sounding frequency higher than the first sounding frequency, of the wireless monitoring system different from the first set of settings and the second set of settings,
        a fourth selectable system state, which is a power saving state, comprises another sub-task different from the particular collection of sub-tasks and a fourth set of settings, comprising a fourth sounding frequency lower than the first sounding frequency, of the wireless monitoring system,
    and
        the processor is capable of switching among the plurality of selectable system states with the corresponding sets of settings of the wireless monitoring system in real time based on a finite state machine (FSM);
    selecting, by the processor, a first one of the selectable system states to be a system state of the wireless monitoring system;
    applying, by the processor, the corresponding set of settings of the system state to configure at least one of: a transmitter, a receiver, a wireless signal, choice of wireless signal, generation and transmission of the wireless signal by the transmitter, reception of the wireless signal by the receiver, coordination of the transmitter and the receiver, transmitting antennas, receiving antennas, carrier frequency, modulation, signal strength, bandwidth, constellation, frequency band, frequency aggregation, frequency hopping, a series of sounding signals in the wireless signal, choice of sounding signals, sounding requirement, sounding frequency, period, timing, rhythm, regularity, signaling, signal format, frame type, field, protocol, standard, management frame, control frame, data frame, management packet, control packet, data packet, frame header and frame body, set of channel information (CI), choice of the CI, set of the CI, obtaining of the CI, respective sub-task, customization of the sub-task, computation for the sub-task, computation based on the CI, monitoring functionality, functionality level, functionality parameter, functionality setting, sensitivity setting, resolution setting, computation requirement, memory requirement, resource constraint, resource management, network congestion management, power management, heat management, computation management, and memory management of the wireless monitoring system;
    transmitting, using the transmitter, the wireless signal through a wireless multipath channel of a venue based on the system state and the applied settings;
    receiving, using the receiver, the wireless signal through the wireless multipath channel based on the system state and the applied settings, wherein the wireless signal is impacted by the wireless multipath channel and a modulation of an object undergoing a motion in the venue;
    obtaining a time series of CI (TSCI) of the wireless multipath channel based on the wireless signal based on the system state and the applied settings;

computing an auto-correlation function (ACF) of the TSCI;

performing the corresponding set of sub-tasks of the system state according to the applied settings based on the ACF of the TSCI; and switching the system state to a second one of the selectable system states based on a result of the corresponding set of sub-tasks and the FSM.

2. The method of claim 1, wherein the first one of the selectable system states is automatically selected to be the system state based on at least one of:
- at least one of: a negotiation, a handshake, or a coordination, between at least two of: the transmitter, the receiver, a server, another transmitter or another receiver;
- at least one of: a constraint, a requirement, or a condition of a sub-task;
- at least one of: a command, a request, a coordination, or a planning of a server;
- a testing procedure; or an optimization criterion.

3. The method of claim 1, further comprising:
updating a setting associated with a particular selectable system state.

4. The method of claim 1, further comprising changing the system state to be an additional one of the selectable system states, wherein the system state is changed based on at least one of:
- a new finite state machine (FSM), a trigger of state transition of the new FSM, a criterion, an event, a condition, a change of the object, a change of the venue, a change of the wireless multipath channel, a new motion of the object to be monitored, a new sub-task, a change of a particular sub-task of the system state, or a new object to be monitored.

5. The method of claim 1, further comprising:
performing each of the corresponding set of sub-tasks of the system state, wherein the venue has a plurality of objects each undergoing a corresponding motion in the venue, wherein each of the corresponding set of sub-tasks comprises monitoring a respective object and the corresponding motion of the respective object based on the TSCI;

changing the system state to a second selectable system state and applying a set of second settings corresponding to the second selectable system state to configure the wireless monitor system;

transmitting, using a second transmitter, a second wireless signal through a second wireless multipath channel of the venue based on the changed system state and the applied second settings;

receiving, using a second receiver, the second wireless signal through the second wireless multipath channel based on the changed system state and the applied second settings, wherein the second wireless signal is impacted by the second wireless multipath channel and a modulation of the plurality of objects each undergoing the respective motion in the venue;

obtaining a second TSCI of the second wireless multipath channel based on the second wireless signal based on the changed system state and the applied second settings;

computing a second ACF of the second TSCI;

performing the corresponding set of sub-tasks of the second selectable system state, wherein each sub-task of the second selectable system state comprises monitoring a respective object and the corresponding motion of the respective object based on the second ACF of the second TSCI.

6. The method of claim 5, further comprising:
determining the system state to be a first selectable system state associated with at least one default sub-task;
changing the system state to be the second selectable system state associated with at least one on-demand sub-task;
changing the system state back to the first selectable system state after finishing the at least one on-demand sub-task.

7. A method for configuring a wireless monitoring system, comprising:
determining, by a processor, a collection of sub-tasks comprising: motion detection, presence detection, proximity detection, object recognition, transient motion monitoring, breathing monitoring, heart beat monitoring, well-being monitoring, counting, fall-down detection, speed measuring, gait recognition, motion recognition, radio biometric based recognition, security event detection, locationing, tracking, navigation, motion localization, distance estimation, angle estimation, material determination, object determination, daily activity monitoring, sleep monitoring, driver sleepiness detection, radio frequency imaging, gesture recognition, keystroke recognition, and handwriting recognition;

determining, by the processor, a plurality of admissible system states of the wireless monitoring system, wherein
each admissible system state comprises a corresponding set of sub-tasks selected from the collection of sub-tasks to be performed by the wireless monitoring system and a corresponding set of settings of the wireless monitoring system for performing the corresponding set of sub-tasks of the task,
a first selectable system state, which is a default state to monitor daily activities of a user, comprises a particular collection of sub-tasks, comprising motion detection and breathing, of the task and a first set of settings, comprising a first sounding frequency, of the wireless monitoring system,
a second selectable system state, which is a low-activity state to monitor the user when sleeping is detected, comprises the particular collection of sub-tasks and a second set of settings, comprising a second sounding frequency lower than the first sounding frequency, of the wireless monitoring system,
a third selectable system state, which is an alarmed state to monitor the user during an alarmed situation, comprises the particular collection of sub-tasks, a sub-task of fall-down detection not in the particular collection, and a third set of settings, comprising a third sounding frequency higher than the first sounding frequency, of the wireless monitoring system different from the first set of settings and the second set of settings,
a fourth selectable system state, which is a power saving state, comprises another sub-task different from the particular collection of sub-tasks and a fourth set of settings, comprising a fourth sounding frequency lower than the first sounding frequency, of the wireless monitoring system, and
the processor is capable of switching among the plurality of admissible system states with the corresponding sets of settings of the wireless monitoring system in real time based on a finite state machine (FSM);
choosing, by the processor, a default admissible system state to be a system state of the wireless monitoring system;
applying, by the processor, a corresponding set of default settings of the default admissible system state to configure at least one of: a transmitter, a receiver, a wireless signal, choice of wireless signal, generation and transmission of the wireless signal by the transmitter, reception of the wireless signal by the receiver, coordination of the transmitter and the receiver, transmitting antennas, receiving antennas, carrier frequency, modulation, signal strength, bandwidth, constellation, frequency band, frequency aggregation, frequency hopping, a series of sounding signals in the wireless signal, choice of sounding signals, sounding requirement, sounding frequency, period, timing, rhythm, regularity, signaling, signal format, frame type, field, protocol, standard, management frame, control frame, data frame, management packet, control packet, data packet, frame header and frame body, set of channel information (CI), choice of the CI, set of the CI, obtaining of the CI, respective sub-task, customization of the sub-task, computation for the sub-task, computation based on the CI, monitoring functionality, functionality level, functionality parameter, functionality setting, sensitivity setting, resolution setting, computation requirement, memory requirement, resource constraint, resource management, network congestion management, power management, heat management, computation management, and memory management of the wireless monitoring system;
transmitting, from the transmitter, the wireless signal through a wireless multipath channel of a venue based on the system state and the applied default settings;
receiving, by the receiver, the wireless signal through the wireless multipath channel based on the system state and the applied default settings, wherein the wireless signal is impacted by the wireless multipath channel and a modulation of an object undergoing a motion in the venue;
obtaining a time series of CI (TSCI) of the wireless multipath channel based on the wireless signal using a processor, a memory and a set of instructions based on the system state and the applied default settings;
computing an auto-correlation function (ACF) of the TSCI;
performing a corresponding set of default sub-tasks of the default admissible system state based on the ACF of the TSCI according to the applied default settings; and
switching the system state to a different admissible system state based on a result of the corresponding set of sub-tasks and the FSM.

8. The method of claim 7, wherein the default admissible system state is automatically chosen to be the system state based on at least one of:
at least one of: a negotiation, a handshake, or a coordination, between at least two of: the transmitter, the receiver, a server, another transmitter or another receiver;
at least one of: a constraint, a requirement, or a condition of a default sub-task;
at least one of: a command, a request, a coordination, or a planning of a server;
a testing procedure; or an optimization criterion.

9. The method of claim 7, further comprising:
performing each of the corresponding set of default sub-tasks of the system state, wherein the venue has a plurality of objects each undergoing a corresponding motion in the venue, wherein each of the corresponding set of default sub-tasks comprises monitoring a respective object and the corresponding motion of the respective object based on the TSCI;
changing the system state to a second admissible system state and applying a set of second settings corresponding to the second admissible system state to configure the wireless monitor system;
transmitting, using a second transmitter, a second wireless signal through a second wireless multipath channel of the venue based on the changed system state and the applied second settings;
receiving, using a second receiver, the second wireless signal through the second wireless multipath channel based on the changed system state and the applied second settings, wherein the second wireless signal is impacted by the second wireless multipath channel and a modulation of the plurality of objects each undergoing the respective motion in the venue;
obtaining a second TSCI of the second wireless multipath channel based on the second wireless signal based on the changed system state and the applied second settings;
computing a second ACF of the second TSCI;
performing the corresponding set of sub-tasks of the second admissible system state, wherein each sub-task of the second admissible system state comprises monitoring a respective object and the corresponding motion of the respective object based on the second ACF of the second TSCI.

10. A wireless monitoring system, comprising:
a processor configured for:
determining a collection of sub-tasks comprising: motion detection, presence detection, proximity detection, object recognition, transient motion monitoring, breathing monitoring, heart beat monitoring, well-being monitoring, counting, fall-down detection, speed measuring, gait recognition, motion recognition, radio biometric based recognition, security event detection, locationing, tracking, navigation, motion localization, distance estimation, angle estimation, material determination, object determination, daily activity monitoring, sleep monitoring, driver sleepiness detection, radio frequency imaging, posture recognition, keystroke recognition, and handwriting recognition;
determining a plurality of selectable system states of the wireless monitoring system, wherein
each selectable system state comprises a corresponding set of sub-tasks selected from the collection of sub-tasks to be performed by the wireless monitoring system and a corresponding set of settings of the wireless monitoring system for performing the corresponding set of sub-tasks of the task,
a first selectable system state, which is a default state to monitor daily activities of a user, comprises a particular collection of sub-tasks, comprising motion detection and breathing, of the task and a first set of settings, comprising a first sounding frequency, of the wireless monitoring system, a second selectable system state, which is a low-activity state to monitor the user when sleeping is detected, comprises the particular collection of sub-tasks and a second set of settings, comprising a second sounding frequency lower than the first sounding frequency, of the wireless monitoring system, a third selectable system state, which is an alarmed state to monitor the user during an alarmed situation, comprises the particular collection of sub-tasks, a sub-task of fall-down detection not in the particular collection, and a third set of settings, comprising a third sounding frequency higher than the first sounding frequency, of the wireless monitoring system different from the first set of settings and the second set of settings, a fourth selectable system state, which is a power saving state, comprises another sub-task different from the particular collection of sub-tasks and a fourth set of settings, comprising a fourth sounding frequency lower than the first sounding frequency, of the wireless monitoring system, and the processor is capable of switching among the plurality of selectable system states with the corresponding sets of settings of the wireless monitoring system in real time based on a finite state machine (FSM), selecting a first one of the selectable system states to be a system state of the wireless monitoring system, and applying the corresponding set of settings of the system state to configure at least one of: a transmitter, a receiver, a wireless signal, choice of wireless signal, generation and transmission of the wireless signal by the transmitter, reception of the wireless signal by the receiver, coordination of the transmitter and the receiver, transmitting antennas, receiving antennas, carrier frequency, modulation, signal strength, bandwidth, constellation, frequency band, frequency aggregation, frequency hopping, a series of sounding signals in the wireless signal, choice of sounding signals, sounding requirement, sounding frequency, period, timing, rhythm, regularity, signaling, signal format, frame type, field, protocol, standard, management frame, control frame, data frame, management packet, control packet, data packet, frame header and frame body, set of channel information (CI), choice of the CI, set of the CI, obtaining of the CI, respective monitoring task, customization of the monitoring task, computation for the monitoring task, computation based on the CI, monitoring functionality, functionality level, functionality parameter, functionality setting, sensitivity setting, resolution setting, computation requirement, memory requirement, resource constraint, resource management, network congestion management, power management, heat management, computation management, and memory management of the wireless monitoring system;

the transmitter configured for transmitting the wireless signal through a wireless multipath channel of a venue based on the system state and the applied settings; and the receiver configured for:
receiving the wireless signal through the wireless multipath channel based on the system state and the applied settings, wherein the wireless signal is impacted by the wireless multipath channel and a modulation of an object undergoing a motion in the venue, obtaining a time series of CI (TSCI) of the wireless multipath channel based on the wireless signal based on the system state and the applied settings, computing an auto-correlation function (ACF) of the TSCI, performing the corresponding set of sub-tasks of the system state according to the applied settings based on the ACF of the TSCI, and switching the system state to a second one of the selectable system states based on a result of the corresponding set of sub-tasks and the FSM.

11. The wireless monitoring system of claim 10, wherein the processor is physically coupled to at least one of: the transmitter, the receiver, a server, another transmitter or another receiver.

12. The wireless monitoring system of claim 10, wherein the one of the selectable system states is chosen to be the system state based on at least one of:
at least one of: a negotiation, a handshake, or a coordination, between at least two of: the transmitter, the receiver, a server, another transmitter or another receiver;
at least one of: a constraint, a requirement, or a condition of a sub-task;
at least one of: a command, a request, a coordination, or a planning of a server;
a testing procedure; or an optimization criterion.

* * * * *